US009913680B2

(12) United States Patent
Voegele et al.

(10) Patent No.: US 9,913,680 B2
(45) Date of Patent: Mar. 13, 2018

(54) SOFTWARE ALGORITHMS FOR ELECTROSURGICAL INSTRUMENTS

(71) Applicant: Ethicon Endo-Surgery, Inc., Cincinnati, OH (US)

(72) Inventors: Aaron C. Voegele, Loveland, OH (US); Kevin L. Houser, Springboro, OH (US); Robert A. Kemerling, Mountain View, CA (US); Gregory A. Trees, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 502 days.

(21) Appl. No.: 14/252,824

(22) Filed: Apr. 15, 2014

(65) Prior Publication Data

US 2015/0289925 A1    Oct. 15, 2015

(51) Int. Cl.
| A61B 18/12 | (2006.01) |
| A61B 18/14 | (2006.01) |
| A61B 18/00 | (2006.01) |
| A61B 90/00 | (2016.01) |
| A61B 34/10 | (2016.01) |

(52) U.S. Cl.
CPC ...... *A61B 18/1445* (2013.01); *A61B 18/1233* (2013.01); *A61B 34/10* (2016.02); *A61B 2018/00196* (2013.01); *A61B 2018/00607* (2013.01); *A61B 2018/00642* (2013.01); *A61B 2018/00791* (2013.01); *A61B 2018/00875* (2013.01); *A61B 2018/00898* (2013.01); *A61B 2018/1455* (2013.01); *A61B 2090/065* (2016.02)

(58) Field of Classification Search
CPC ........ A61B 2018/875; A61B 2018/898; A61B 2018/904
See application file for complete search history.

(56) References Cited

U.S. PATENT DOCUMENTS

| 2,366,274 A | 1/1945 | Luth et al. |
| 2,458,152 A | 1/1949 | Eakins |
| 2,510,693 A | 6/1950 | Green |

(Continued)

FOREIGN PATENT DOCUMENTS

| CN | 2868227 Y | 2/2007 |
| DE | 4300307 A1 | 7/1994 |

(Continued)

OTHER PUBLICATIONS

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

(Continued)

*Primary Examiner* — Ronald Hupczey, Jr.

(57) ABSTRACT

A surgical system includes a module for compiling a plurality of operational parameters of the surgical system during a plurality of treatment cycles performed by the surgical system. The module includes a processor and a memory unit, the processor configured to store in the memory unit values of the plurality of operational parameters associated with each of the plurality of treatment cycles, wherein the processor is configured to identify a subset of the stored values of the plurality of operational parameters temporally proximate to an intervening event.

20 Claims, 18 Drawing Sheets

(56) References Cited

U.S. PATENT DOCUMENTS

| | | |
|---|---|---|
| 2,867,039 A | 1/1959 | Zach |
| 3,166,971 A | 1/1965 | Stoecker |
| 3,525,912 A | 8/1970 | Wallin |
| 3,580,841 A | 5/1971 | Cadotte et al. |
| 3,703,651 A | 11/1972 | Blowers |
| 3,777,760 A | 12/1973 | Essner |
| 4,005,714 A | 2/1977 | Hiltebrandt |
| 4,034,762 A | 7/1977 | Cosens et al. |
| 4,058,126 A | 11/1977 | Leveen |
| 4,203,430 A | 5/1980 | Takahashi |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,463,759 A | 8/1984 | Garito et al. |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,617,927 A | 10/1986 | Manes |
| 4,735,603 A | 4/1988 | Goodson et al. |
| 4,761,871 A | 8/1988 | O'Connor et al. |
| 4,830,462 A | 5/1989 | Karny et al. |
| 4,849,133 A | 7/1989 | Yoshida et al. |
| 4,860,745 A | 8/1989 | Farin et al. |
| 4,878,493 A | 11/1989 | Pasternak et al. |
| 4,880,015 A | 11/1989 | Nierman |
| 4,910,389 A | 3/1990 | Sherman et al. |
| 4,920,978 A | 5/1990 | Colvin |
| 4,936,842 A | 6/1990 | D'Amelio et al. |
| 5,020,514 A | 6/1991 | Heckele |
| 5,061,269 A | 10/1991 | Muller |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,156,633 A | 10/1992 | Smith |
| 5,160,334 A | 11/1992 | Billings et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,217,460 A | 6/1993 | Knoepfler |
| 5,234,428 A | 8/1993 | Kaufman |
| 5,258,006 A | 11/1993 | Rydell et al. |
| 5,285,945 A | 2/1994 | Brinkerhoff et al. |
| 5,290,286 A | 3/1994 | Parins |
| 5,309,927 A | 5/1994 | Welch |
| 5,312,023 A | 5/1994 | Green et al. |
| 5,318,563 A | 6/1994 | Malis et al. |
| 5,318,564 A | 6/1994 | Eggers |
| 5,318,589 A | 6/1994 | Lichtman |
| 5,326,013 A | 7/1994 | Green et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,361,583 A | 11/1994 | Huitema |
| 5,383,874 A | 1/1995 | Jackson et al. |
| 5,387,207 A | 2/1995 | Dyer et al. |
| 5,389,098 A | 2/1995 | Tsuruta et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,417,709 A | 5/1995 | Slater |
| 5,428,504 A | 6/1995 | Bhatla |
| 5,429,131 A | 7/1995 | Scheinman et al. |
| 5,443,463 A | 8/1995 | Stern et al. |
| 5,445,638 A | 8/1995 | Rydell et al. |
| 5,451,227 A | 9/1995 | Michaelson |
| 5,456,684 A | 10/1995 | Schmidt et al. |
| 5,458,598 A | 10/1995 | Feinberg et al. |
| 5,465,895 A | 11/1995 | Knodel et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,484,436 A | 1/1996 | Eggers et al. |
| 5,486,189 A | 1/1996 | Mudry et al. |
| 5,496,317 A | 3/1996 | Goble et al. |
| 5,504,650 A | 4/1996 | Katsui et al. |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,681 A * | 7/1996 | Strul ................ A61B 18/1206 606/1 |
| 5,542,916 A | 8/1996 | Hirsch et al. |
| 5,558,671 A | 9/1996 | Yates |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,607,450 A | 3/1997 | Zvenyatsky et al. |
| 5,611,813 A | 3/1997 | Lichtman |
| 5,618,307 A | 4/1997 | Donlon et al. |
| 5,624,452 A | 4/1997 | Yates |
| 5,632,432 A | 5/1997 | Schulze et al. |
| 5,647,871 A | 7/1997 | Levine et al. |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,674,219 A | 10/1997 | Monson et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A * | 2/1998 | Zacharias ............ A61B 17/29 606/1 |
| 5,720,744 A * | 2/1998 | Eggleston .......... A61B 18/1206 606/38 |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,811 A | 9/1998 | Yates et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman |
| 5,836,909 A | 11/1998 | Cosmescu |
| 5,836,943 A | 11/1998 | Miller, III |
| 5,836,990 A | 11/1998 | Li |
| 5,853,412 A | 12/1998 | Mayenberger |
| 5,876,401 A | 3/1999 | Schulze et al. |
| 5,878,193 A | 3/1999 | Wang et al. |
| 5,880,668 A | 3/1999 | Hall |
| 5,891,142 A | 4/1999 | Eggers et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,984,938 A | 11/1999 | Yoon |

(56) References Cited

U.S. PATENT DOCUMENTS

| | | |
|---|---|---|
| 6,003,517 A | 12/1999 | Sheffield et al. |
| 6,013,052 A | 1/2000 | Durman et al. |
| 6,024,741 A | 2/2000 | Williamson, IV et al. |
| 6,024,744 A | 2/2000 | Kese et al. |
| 6,033,399 A | 3/2000 | Gines |
| 6,039,734 A | 3/2000 | Goble |
| 6,050,996 A | 4/2000 | Schmaltz et al. |
| 6,063,098 A | 5/2000 | Houser et al. |
| 6,068,629 A | 5/2000 | Haissaguerre et al. |
| 6,074,389 A | 6/2000 | Levine et al. |
| 6,091,995 A | 7/2000 | Ingle et al. |
| 6,099,483 A | 8/2000 | Palmer et al. |
| 6,099,550 A | 8/2000 | Yoon |
| H1904 H | 10/2000 | Yates et al. |
| 6,132,368 A | 10/2000 | Cooper |
| 6,144,402 A | 11/2000 | Norsworthy et al. |
| 6,152,923 A | 11/2000 | Ryan |
| 6,154,198 A | 11/2000 | Rosenberg |
| 6,162,208 A | 12/2000 | Hipps |
| 6,174,309 B1 | 1/2001 | Wrublewski et al. |
| 6,176,857 B1 | 1/2001 | Ashley |
| 6,190,386 B1 | 2/2001 | Rydell |
| 6,206,876 B1 | 3/2001 | Levine et al. |
| 6,228,080 B1 | 5/2001 | Gines |
| 6,231,565 B1 | 5/2001 | Tovey et al. |
| 6,259,230 B1 | 7/2001 | Chou |
| 6,277,117 B1 | 8/2001 | Tetzlaff et al. |
| 6,292,700 B1 | 9/2001 | Morrison et al. |
| 6,325,799 B1 | 12/2001 | Goble |
| 6,340,878 B1 | 1/2002 | Oglesbee |
| 6,364,888 B1 | 4/2002 | Niemeyer et al. |
| 6,387,109 B1 | 5/2002 | Davison et al. |
| 6,391,026 B1 | 5/2002 | Hung et al. |
| 6,398,779 B1 | 6/2002 | Buysse et al. |
| H2037 H | 7/2002 | Yates et al. |
| 6,419,675 B1 | 7/2002 | Gallo, Sr. |
| 6,430,446 B1 | 8/2002 | Knowlton |
| 6,443,968 B1 | 9/2002 | Holthaus et al. |
| 6,458,128 B1 | 10/2002 | Schulze |
| 6,464,689 B1 | 10/2002 | Qin et al. |
| 6,464,702 B2 | 10/2002 | Schulze et al. |
| 6,480,796 B2 | 11/2002 | Wiener |
| 6,491,690 B1 | 12/2002 | Goble et al. |
| 6,500,112 B1 | 12/2002 | Khouri |
| 6,500,176 B1 | 12/2002 | Truckai et al. |
| 6,503,248 B1 | 1/2003 | Levine |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,551,309 B1 | 4/2003 | LePivert |
| 6,554,829 B2 | 4/2003 | Schulze et al. |
| 6,558,376 B2 | 5/2003 | Bishop |
| 6,562,037 B2 * | 5/2003 | Paton ............... A61B 18/1442 606/51 |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,602,252 B2 | 8/2003 | Mollenauer |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,644,532 B2 | 11/2003 | Green et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,733,498 B2 | 5/2004 | Paton et al. |
| 6,746,443 B1 | 6/2004 | Morley et al. |
| 6,752,815 B2 | 6/2004 | Beaupre |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,775,575 B2 | 8/2004 | Bommannan et al. |
| 6,783,524 B2 | 8/2004 | Anderson et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 6,977,495 B2 | 12/2005 | Donofrio |
| 6,994,709 B2 | 2/2006 | Iida |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,077,853 B2 | 7/2006 | Kramer et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,273,483 B2 | 9/2007 | Wiener et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |

(56) References Cited

U.S. PATENT DOCUMENTS

| | | | |
|---|---|---|---|
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,384,420 B2 | 6/2008 | Dycus et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,416,101 B2 | 8/2008 | Shelton, IV et al. |
| 7,422,139 B2 | 9/2008 | Shelton, IV et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,506,791 B2 | 3/2009 | Omaits et al. |
| 7,510,107 B2 | 3/2009 | Timm et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,540,872 B2 | 6/2009 | Schechter et al. |
| 7,543,730 B1 | 6/2009 | Marczyk |
| 7,550,216 B2 | 6/2009 | Ofer et al. |
| 7,553,309 B2 * | 6/2009 | Buysse ............. A61B 18/1206 606/34 |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,621,930 B2 | 11/2009 | Houser |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,691,095 B2 | 4/2010 | Bednarek et al. |
| 7,691,098 B2 | 4/2010 | Wallace et al. |
| 7,703,459 B2 | 4/2010 | Saadat et al. |
| 7,703,653 B2 | 4/2010 | Shah et al. |
| 7,708,751 B2 | 5/2010 | Hughes et al. |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,726,537 B2 | 6/2010 | Olson et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,210 B2 | 8/2010 | Shelton, IV et al. |
| 7,766,910 B2 | 8/2010 | Hixson et al. |
| 7,770,775 B2 | 8/2010 | Shelton, IV et al. |
| 7,775,972 B2 | 8/2010 | Brock et al. |
| 7,776,037 B2 | 8/2010 | Odom |
| 7,780,651 B2 | 8/2010 | Madhani et al. |
| 7,780,663 B2 | 8/2010 | Yates et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,803,156 B2 | 9/2010 | Eder et al. |
| 7,806,891 B2 | 10/2010 | Nowlin et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,819,872 B2 | 10/2010 | Johnson et al. |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,861,906 B2 | 1/2011 | Doll et al. |
| 7,879,035 B2 | 2/2011 | Garrison et al. |
| 7,879,070 B2 | 2/2011 | Ortiz et al. |
| 7,896,875 B2 | 3/2011 | Heim et al. |
| 7,901,400 B2 | 3/2011 | Wham et al. |
| 7,909,220 B2 | 3/2011 | Viola |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,649 B2 | 4/2011 | Couture et al. |
| 7,935,114 B2 | 5/2011 | Takashino et al. |
| 7,951,165 B2 | 5/2011 | Golden et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,038,693 B2 | 10/2011 | Allen |
| 8,056,720 B2 | 11/2011 | Hawkes |
| 8,058,771 B2 | 11/2011 | Giordano et al. |
| 8,061,014 B2 | 11/2011 | Smith et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,221,415 B2 | 7/2012 | Francischelli |
| 8,236,020 B2 | 8/2012 | Smith et al. |
| 8,241,235 B2 | 8/2012 | Kahler et al. |
| 8,241,284 B2 | 8/2012 | Dycus et al. |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,267,300 B2 | 9/2012 | Boudreaux |
| 8,277,446 B2 | 10/2012 | Heard |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,357,158 B2 | 1/2013 | McKenna et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,397,971 B2 | 3/2013 | Yates et al. |
| 8,403,948 B2 | 3/2013 | Deville et al. |
| 8,403,949 B2 | 3/2013 | Palmer et al. |

(56) References Cited

U.S. PATENT DOCUMENTS

| | | |
|---|---|---|
| 8,403,950 B2 | 3/2013 | Palmer et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,430,876 B2 | 4/2013 | Kappus et al. |
| 8,435,257 B2 | 5/2013 | Smith et al. |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,496,682 B2 | 7/2013 | Guerra et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| D695,407 S | 12/2013 | Price et al. |
| 8,613,383 B2 | 12/2013 | Beckman et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,638,428 B2 | 1/2014 | Brown |
| 8,647,350 B2 | 2/2014 | Mohan et al. |
| 8,663,220 B2 | 3/2014 | Wiener et al. |
| 8,663,222 B2 | 3/2014 | Anderson et al. |
| 8,684,253 B2 | 4/2014 | Giordano et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,827,992 B2 | 9/2014 | Koss et al. |
| 8,834,466 B2 | 9/2014 | Cummings et al. |
| 8,834,518 B2 | 9/2014 | Faller et al. |
| 8,845,630 B2 | 9/2014 | Mehta et al. |
| 8,888,776 B2 | 11/2014 | Dietz et al. |
| 8,888,809 B2 | 11/2014 | Davison et al. |
| 8,906,016 B2 | 12/2014 | Boudreaux et al. |
| 8,926,607 B2 | 1/2015 | Norvell et al. |
| 8,926,608 B2 | 1/2015 | Bacher et al. |
| 8,931,682 B2 | 1/2015 | Timm et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,992,422 B2 | 3/2015 | Spivey et al. |
| 9,005,199 B2 | 4/2015 | Beckman et al. |
| 9,011,437 B2 | 4/2015 | Woodruff et al. |
| 9,028,494 B2 | 5/2015 | Shelton, IV et al. |
| 9,028,519 B2 | 5/2015 | Yates et al. |
| 9,044,243 B2 | 6/2015 | Johnson et al. |
| 9,044,256 B2 | 6/2015 | Cadeddu et al. |
| 9,055,961 B2 | 6/2015 | Manzo et al. |
| 9,060,770 B2 | 6/2015 | Shelton, IV et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,101,385 B2 | 8/2015 | Shelton, IV et al. |
| 9,119,657 B2 | 9/2015 | Shelton, IV et al. |
| 9,125,662 B2 | 9/2015 | Shelton, IV |
| 9,149,324 B2 | 10/2015 | Huang et al. |
| 9,149,325 B2 | 10/2015 | Worrell et al. |
| 9,168,085 B2 | 10/2015 | Juzkiw et al. |
| 9,179,912 B2 | 11/2015 | Yates et al. |
| 9,192,380 B2 | 11/2015 | Racenet et al. |
| 9,192,431 B2 | 11/2015 | Woodruff et al. |
| 9,198,714 B2 | 12/2015 | Worrell et al. |
| 9,204,879 B2 | 12/2015 | Shelton, IV |
| 9,216,050 B2 | 12/2015 | Condie et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,259,265 B2 | 2/2016 | Harris et al. |
| 9,265,926 B2 | 2/2016 | Strobl et al. |
| 9,277,962 B2 | 3/2016 | Koss et al. |
| 9,283,027 B2 | 3/2016 | Monson et al. |
| 9,283,045 B2 | 3/2016 | Rhee et al. |
| 9,295,514 B2 | 3/2016 | Shelton, IV et al. |
| 9,314,292 B2 | 4/2016 | Trees et al. |
| 9,326,788 B2 | 5/2016 | Batross et al. |
| 9,333,025 B2 | 5/2016 | Monson et al. |
| 9,351,754 B2 | 5/2016 | Vakharia et al. |
| 9,375,232 B2 | 6/2016 | Hunt et al. |
| 9,375,267 B2 | 6/2016 | Kerr et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,510,906 B2 | 12/2016 | Boudreaux et al. |
| 2002/0022836 A1 | 2/2002 | Goble et al. |
| 2002/0049551 A1* | 4/2002 | Friedman ....... A61B 17/320068 702/65 |
| 2002/0107517 A1 | 8/2002 | Witt et al. |
| 2002/0165541 A1 | 11/2002 | Whitman |
| 2003/0014053 A1 | 1/2003 | Nguyen et al. |
| 2003/0105474 A1 | 6/2003 | Bonutti |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0054364 A1 | 3/2004 | Aranyi et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193148 A1 | 9/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0103819 A1 | 5/2005 | Racenet et al. |
| 2005/0131390 A1 | 6/2005 | Heinrich et al. |
| 2005/0165429 A1 | 7/2005 | Douglas et al. |

(56) References Cited

U.S. PATENT DOCUMENTS

| | | |
|---|---|---|
| 2005/0171522 A1 | 8/2005 | Christopherson |
| 2005/0203507 A1 | 9/2005 | Truckai et al. |
| 2005/0256405 A1 | 11/2005 | Makin et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0058825 A1 | 3/2006 | Ogura et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0106317 A1 | 5/2007 | Shelton, IV et al. |
| 2007/0118115 A1 | 5/2007 | Artale et al. |
| 2007/0146113 A1 | 6/2007 | Truckai et al. |
| 2007/0173803 A1 | 7/2007 | Wham et al. |
| 2007/0173811 A1 | 7/2007 | Couture et al. |
| 2007/0173813 A1 | 7/2007 | Odom |
| 2007/0175949 A1 | 8/2007 | Shelton, IV et al. |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0208340 A1 | 9/2007 | Ganz et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2007/0265616 A1 | 11/2007 | Couture et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0214967 A1 | 9/2008 | Aranyi et al. |
| 2008/0221565 A1 | 9/2008 | Eder et al. |
| 2008/0255642 A1 | 10/2008 | Zarins et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2008/0300588 A1* | 12/2008 | Groth ............... A61B 18/1206 606/34 |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0099582 A1 | 4/2009 | Isaacs et al. |
| 2009/0112229 A1 | 4/2009 | Omori et al. |
| 2009/0125026 A1 | 5/2009 | Rioux et al. |
| 2009/0125027 A1 | 5/2009 | Fischer |
| 2009/0131929 A1 | 5/2009 | Shimizu |
| 2009/0138003 A1 | 5/2009 | Deville et al. |
| 2009/0138006 A1 | 5/2009 | Bales et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0248021 A1 | 10/2009 | McKenna |
| 2009/0254080 A1 | 10/2009 | Honda |
| 2009/0287205 A1 | 11/2009 | Ingle |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1* | 1/2011 | DiNardo ............ A61B 17/320092 606/34 |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0118754 A1 | 5/2011 | Dachs, II et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295269 A1 | 12/2011 | Swensgard et al. |
| 2011/0295295 A1 | 12/2011 | Shelton, IV et al. |
| 2011/0301605 A1 | 12/2011 | Homer |
| 2011/0306967 A1 | 12/2011 | Payne et al. |
| 2011/0313415 A1 | 12/2011 | Fernandez et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116265 A1 | 5/2012 | Houser et al. |
| 2012/0116379 A1 | 5/2012 | Yates et al. |
| 2012/0116380 A1 | 5/2012 | Madan et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0138660 A1 | 6/2012 | Shelton, IV |
| 2012/0150170 A1 | 6/2012 | Buysse et al. |
| 2012/0150192 A1 | 6/2012 | Dachs, II et al. |
| 2012/0172859 A1 | 7/2012 | Condie et al. |
| 2012/0265196 A1 | 10/2012 | Turner et al. |
| 2012/0265241 A1 | 10/2012 | Hart et al. |
| 2012/0296371 A1 | 11/2012 | Kappus et al. |
| 2012/0323238 A1 | 12/2012 | Tyrrell et al. |
| 2013/0023925 A1 | 1/2013 | Mueller |
| 2013/0030428 A1 | 1/2013 | Worrell et al. |
| 2013/0030433 A1 | 1/2013 | Heard |
| 2013/0035685 A1 | 2/2013 | Fischer et al. |
| 2013/0079762 A1 | 3/2013 | Twomey et al. |
| 2013/0085496 A1 | 4/2013 | Unger et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0253256 A1 | 9/2013 | Griffith et al. |
| 2013/0253502 A1 | 9/2013 | Aronow et al. |
| 2013/0296843 A1 | 11/2013 | Boudreaux et al. |
| 2013/0338661 A1 | 12/2013 | Behnke, II |

(56) References Cited

U.S. PATENT DOCUMENTS

| | | |
|---|---|---|
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0094801 A1 | 4/2014 | Boudreaux et al. |
| 2014/0194875 A1 | 4/2014 | Reschke et al. |
| 2014/0180281 A1 | 6/2014 | Rusin |
| 2014/0194874 A1 | 7/2014 | Dietz et al. |
| 2014/0194915 A1 | 7/2014 | Johnson et al. |
| 2014/0214019 A1 | 7/2014 | Baxter, III et al. |
| 2014/0228844 A1 | 8/2014 | Hörlle et al. |
| 2014/0257284 A1 | 9/2014 | Artale |
| 2014/0303551 A1 | 10/2014 | Germain et al. |
| 2014/0316408 A1 | 10/2014 | Davison et al. |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133929 A1 | 5/2015 | Evans et al. |
| 2015/0141981 A1 | 5/2015 | Price et al. |
| 2015/0190189 A1 | 7/2015 | Yates et al. |
| 2015/0196352 A1 | 7/2015 | Beckman et al. |
| 2015/0230853 A1 | 8/2015 | Johnson et al. |
| 2015/0230861 A1 | 8/2015 | Woloszko et al. |
| 2015/0265347 A1 | 9/2015 | Yates et al. |
| 2015/0272602 A1 | 10/2015 | Boudreaux et al. |
| 2015/0272657 A1 | 10/2015 | Yates et al. |
| 2015/0272659 A1 | 10/2015 | Boudreaux et al. |
| 2015/0272660 A1 | 10/2015 | Boudreaux et al. |
| 2015/0289925 A1 | 10/2015 | Voegele et al. |
| 2015/0297286 A1 | 10/2015 | Boudreaux et al. |
| 2016/0045248 A1 | 2/2016 | Unger et al. |
| 2016/0051315 A1 | 2/2016 | Boudreaux |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0128762 A1 | 5/2016 | Harris et al. |
| 2016/0135875 A1 | 5/2016 | Strobl et al. |
| 2016/0157927 A1 | 6/2016 | Corbett et al. |
| 2016/0175024 A1 | 6/2016 | Yates et al. |
| 2016/0175028 A1 | 6/2016 | Trees et al. |
| 2016/0175029 A1 | 6/2016 | Witt et al. |
| 2016/0175030 A1 | 6/2016 | Boudreaux |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0228171 A1 | 8/2016 | Boudreaux |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |
| 2016/0317215 A1 | 11/2016 | Worrell et al. |

FOREIGN PATENT DOCUMENTS

| | | |
|---|---|---|
| DE | 19608716 C1 | 4/1997 |
| DE | 29623113 U1 | 10/1997 |
| DE | 20004812 U1 | 9/2000 |
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0557806 B1 | 5/1998 |
| EP | 0640317 B1 | 9/1999 |
| EP | 0722696 B1 | 12/2002 |
| EP | 1293172 B1 | 4/2006 |
| EP | 0875209 B1 | 5/2006 |
| EP | 1704824 A1 | 9/2006 |
| EP | 1749479 A1 | 2/2007 |
| EP | 1767157 A1 | 3/2007 |
| EP | 1254637 B1 | 8/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1435852 B1 | 12/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1510178 B1 | 6/2011 |
| EP | 1728475 B1 | 8/2011 |
| EP | 2353518 A1 | 8/2011 |
| EP | 2529681 A1 | 12/2012 |
| EP | 1767164 B1 | 1/2013 |
| EP | 2316359 B1 | 3/2013 |
| EP | 2578172 A2 | 4/2013 |
| GB | 2508143 B1 | 2/2014 |
| GB | 2472216 A | 2/2011 |
| JP | H 08-229050 A | 9/1996 |
| JP | 2008-018226 A | 1/2008 |
| JP | 5714508 B2 | 5/2015 |
| WO | WO 81/03272 A1 | 11/1981 |
| WO | WO 93/07817 A1 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40857 A1 | 8/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/062241 A1 | 8/2002 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/032754 A2 | 4/2004 |

(56) References Cited

FOREIGN PATENT DOCUMENTS

| WO | WO 2004/032762 A1 | 4/2004 |
|---|---|---|
| WO | WO 2004/032763 A2 | 4/2004 |
| WO | WO 2004/078051 A2 | 9/2004 |
| WO | WO 2004/112618 A2 | 12/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2006/119139 A2 | 11/2006 |
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/008672 A2 | 1/2011 |
| WO | WO 2011/084768 A1 | 7/2011 |
| WO | WO 2011/089717 A1 | 7/2011 |
| WO | WO 2011/144911 A1 | 11/2011 |
| WO | WO 2012/044606 A2 | 4/2012 |
| WO | WO 2012/166510 A1 | 12/2012 |
| WO | WO 2013/034629 A1 | 3/2013 |
| WO | WO 2013/062978 A2 | 5/2013 |
| WO | WO 2013/102602 A2 | 7/2013 |
| WO | WO 2013/154157 A1 | 10/2013 |
| WO | WO 2015/197395 A8 | 12/2015 |

OTHER PUBLICATIONS

Hörmann et al., "Reversible and irreversible denaturation of collagen fibers." Biochemistry, 10, pp. 932-937 (1971).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-induced changes in the mechanics of a collagenous tissue: pseudoelastic behavior at 37° C.," Journal of Biomechanics, 31, pp. 211-216 (1998).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
Glaser and Subak-Sharpe, *Integrated Circuit Engineering*, Addison-Wesley Publishing, Reading, MA (1979). (book—not attached).
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Covidien Brochure, The LigaSure Precise™ Instrument, dated Mar. 2011 (2 pages).
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S_D027541.
Jang, J. et al. "Neuro-fuzzy and Soft Computing." Prentice Hall, 1997, pp. 13-89, 199-293, 335-393,453-496, 535-549.
Douglas, S.C. "Introduction to Adaptive Filter". Digital Signal Processing Handbook. Ed. Vijay K. Madisetti and Douglas B. Williams. Boca Raton: CRC Press LLC, 1999.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for No. Of Strands in a Litz-Wire Transformer Winding," IEEE Transactions on Power Electronics, vol. 14, No. 2, Mar. 1999, pp. 283-291.
https://www.kjnnagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
U.S. Appl. No. 15/265,293, filed Sep. 14, 2016.
U.S. Appl. No. 15/258,570, filed Sep. 7, 2016.
U.S. Appl. No. 15/258,578, filed Sep. 7, 2016.
U.S. Appl. No. 15/258,586, filed Sep. 7, 2016.
U.S. Appl. No. 15/258,598, filed Sep. 7, 2016.
U.S. Appl. No. 12/576,529, filed Oct. 9, 2009.
International Preliminary Report on Patentability for PCT/US2015/025890 dated Oct. 18, 2016 (5 pages).
International Search Report for PCT/US2015/025890 dated Jul. 10, 2015 (4 pages).

\* cited by examiner

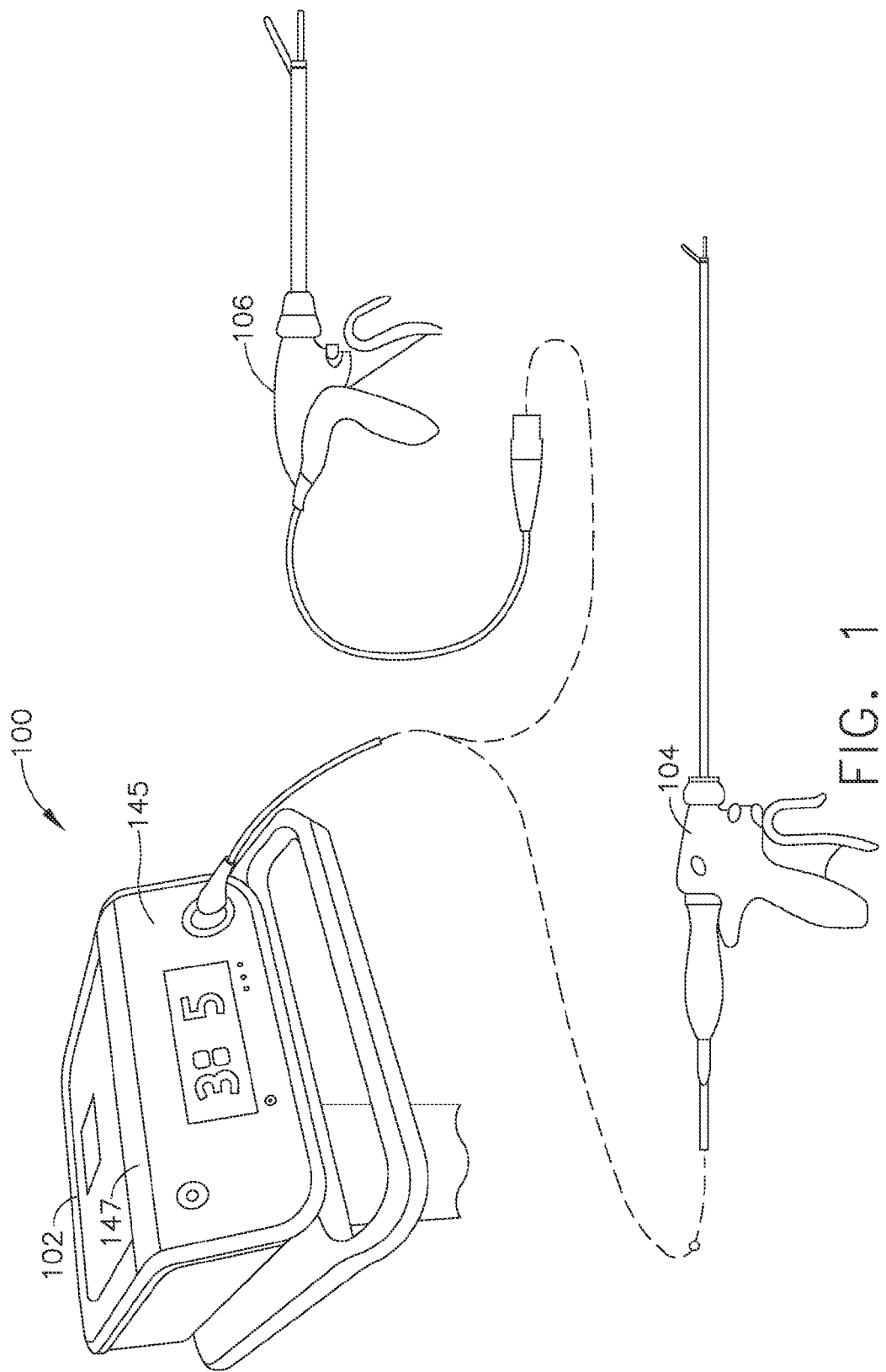

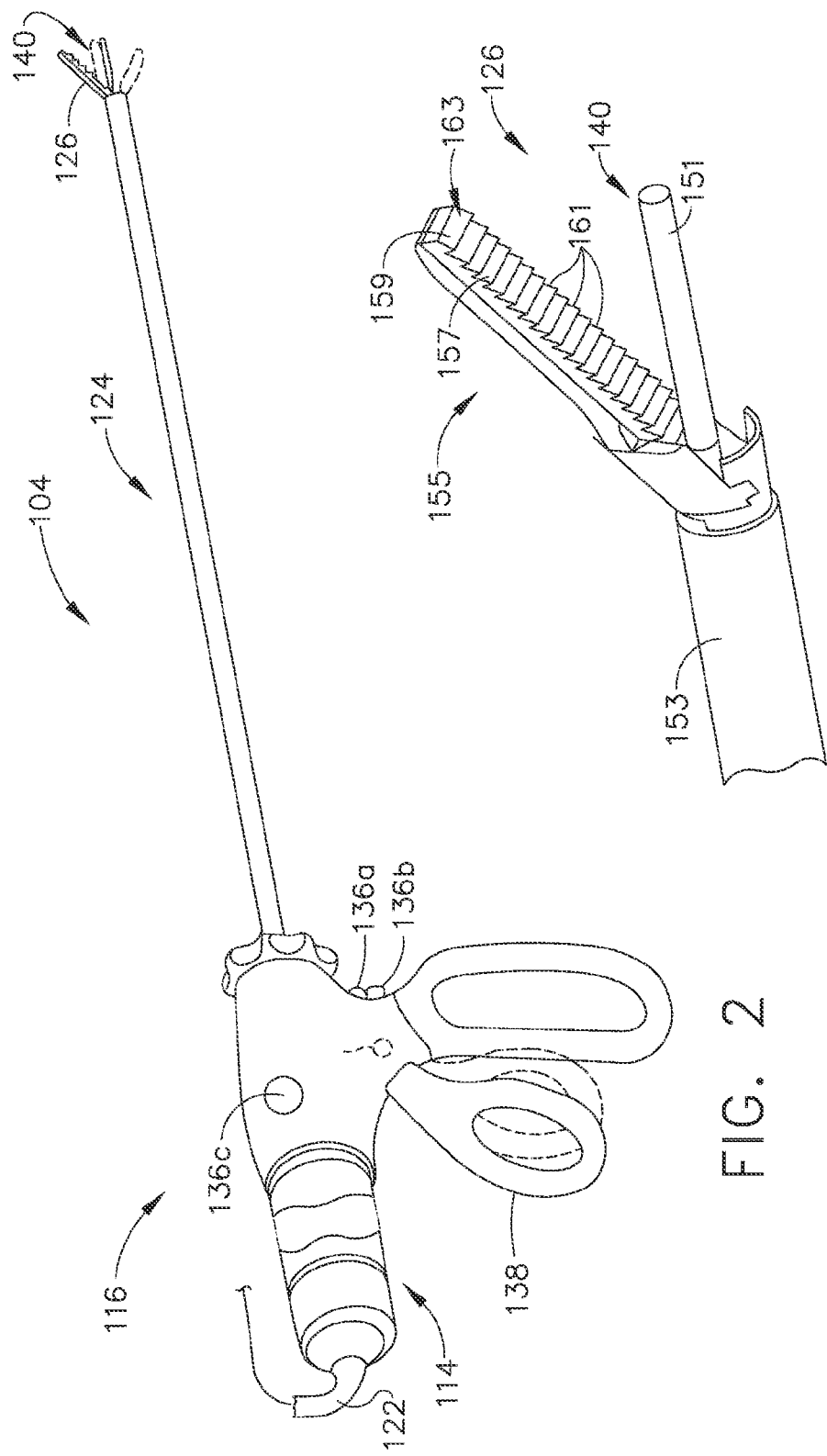

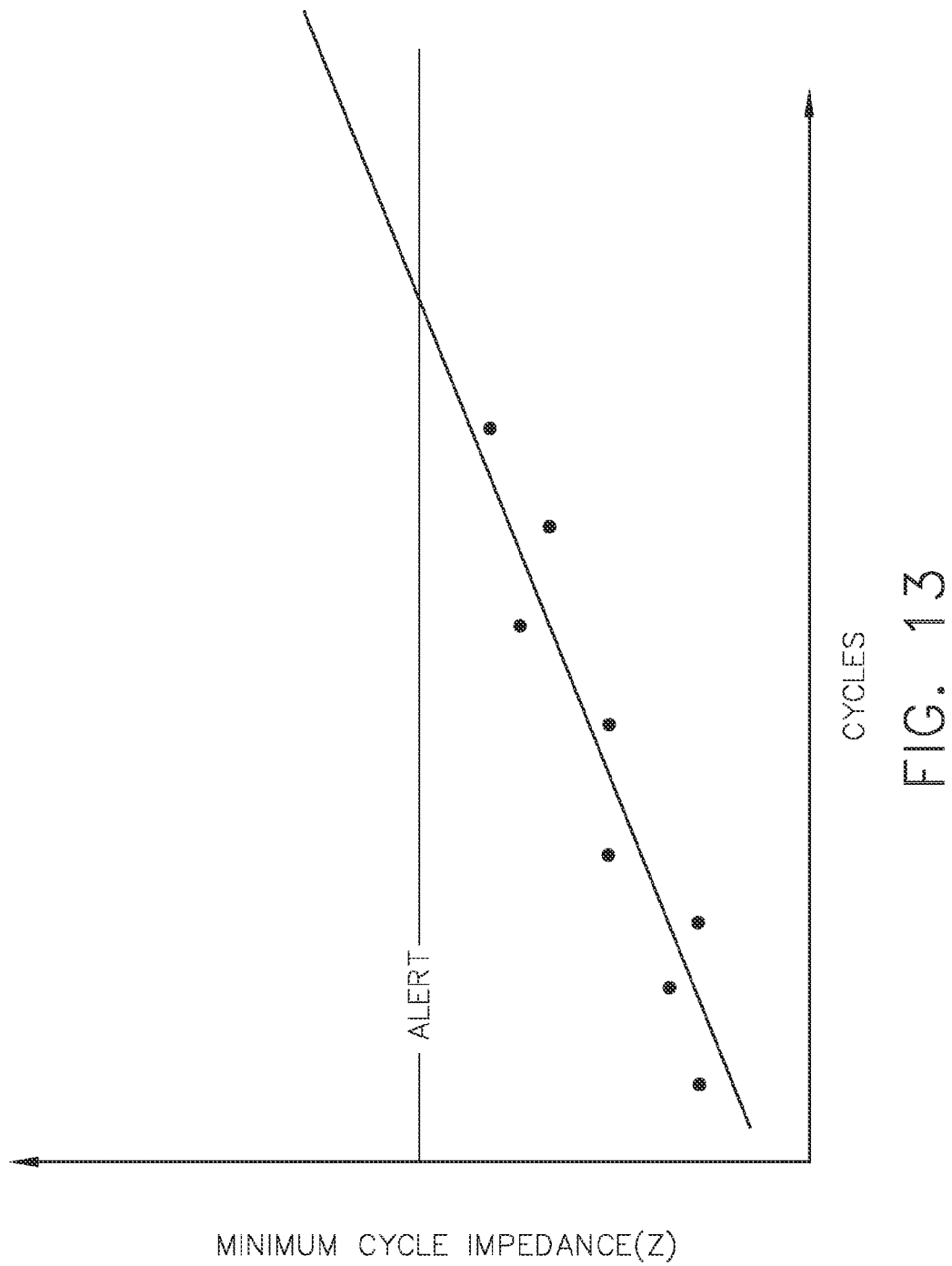

| TREATMENT CYCLE # | CURRENT (I) | VOLTAGE (V) | TISSUE IMPEDANCE (Z) | MINIMUM TISSUE IMPEDANCE ($Z_{min}$) | ENERGY DELIVERED (E) | PEAK POWER (PP) | CYCLE TIME (T) | TISSUE TYPE | PROCEDURE TYPE | PROCEDURE TIME (PT) | TOTAL TIME OF OPERATION (OT) | USER INFO. |
|---|---|---|---|---|---|---|---|---|---|---|---|---|
| C1 | I1 | V1 | Z1 | $Z_{min1}$ | E1 | PP1 | T1 | TYPE1 | TYPE1 | PT1 | OT1 | U1 |
| C2 | I2 | V2 | Z2 | $Z_{min2}$ | E2 | PP2 | T2 | TYPE2 | TYPE2 | PT2 | OT2 | U2 |
| C3 | I3 | V3 | Z3 | $Z_{min3}$ | E3 | PP3 | T3 | TYPE3 | TYPE3 | PT3 | OT3 | U3 |
| C4 | I4 | V4 | Z4 | $Z_{min4}$ | E4 | PP4 | T4 | TYPE4 | TYPE4 | PT4 | OT4 | U4 |
| C5 | I5 | V5 | Z5 | $Z_{min5}$ | E5 | PP5 | T5 | TYPE5 | TYPE5 | PT5 | OT5 | U5 |
| Cn | In | Vn | Zn | $(Z_{min})n$ | En | PPn | Tn | (TYPE)n | (TYPE)n | PTn | OTn | Un |

FIG. 14

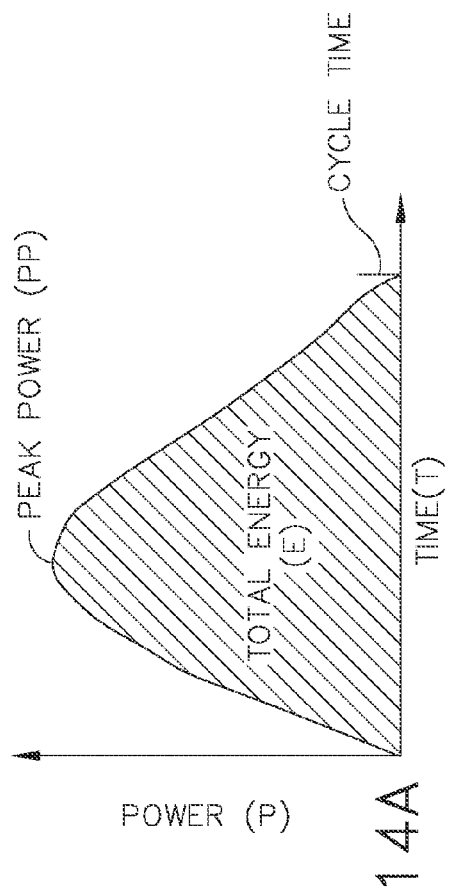

FIG. 14A

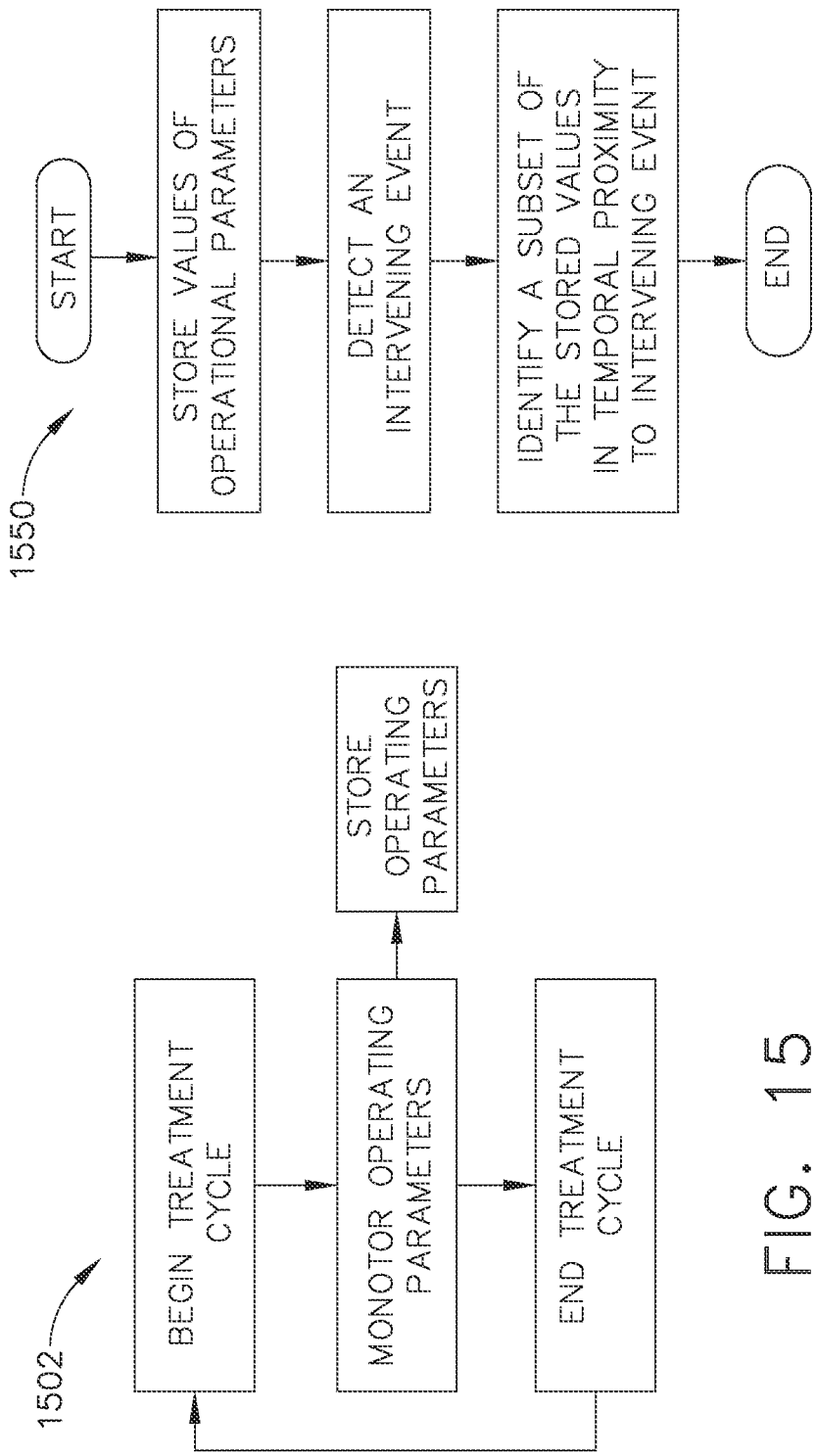

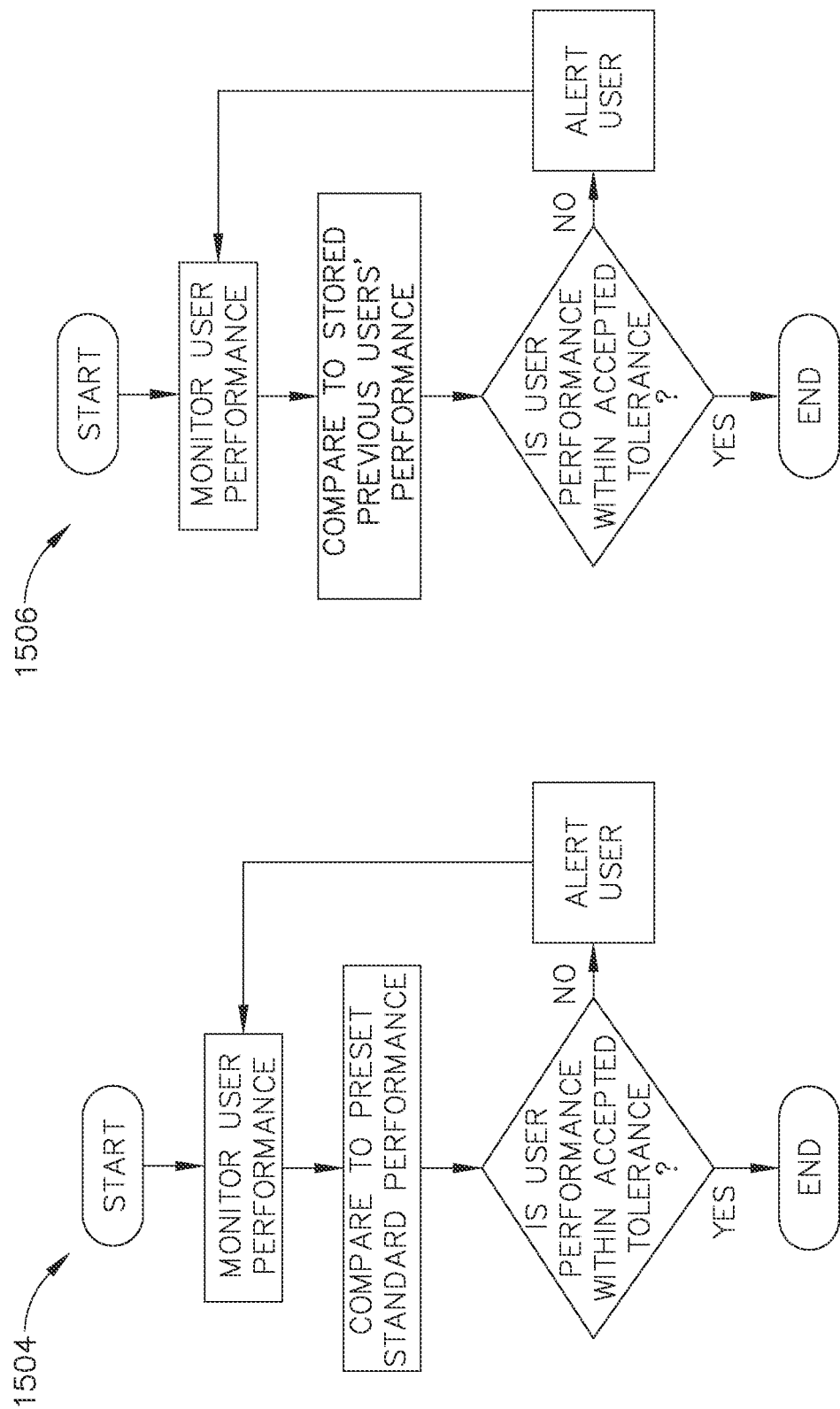

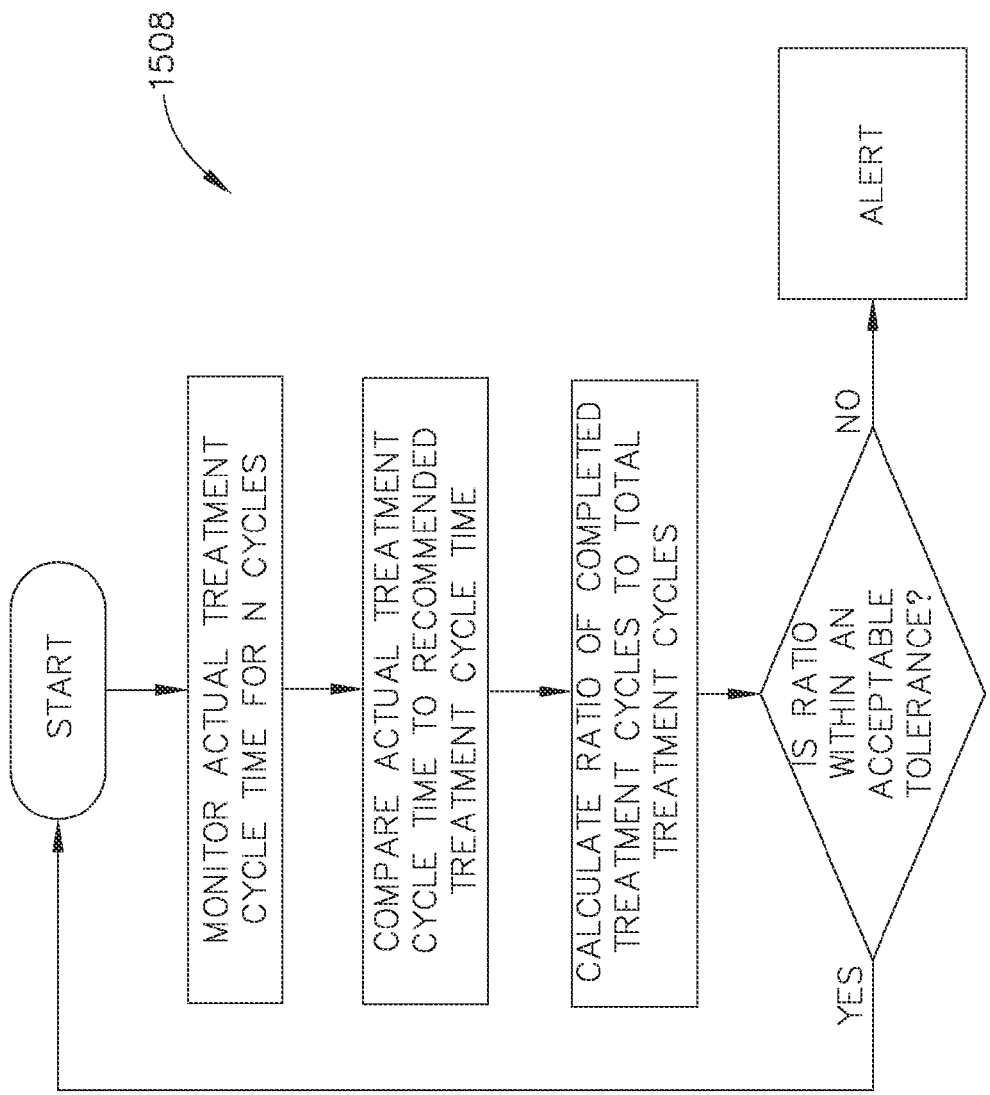

SOFTWARE ALGORITHMS FOR ELECTROSURGICAL INSTRUMENTS

BACKGROUND

The present disclosure relates to surgical instruments and generators for supplying energy to surgical instruments, for use in open or minimally invasive surgical environments.

In various open, endoscopic, and/or laparoscopic surgeries, for example, it may be desirable to coagulate, seal, and/or fuse tissue. One method of sealing tissue relies upon the application of energy to tissue captured or clamped within an end effector or an end-effector assembly of a surgical instrument in order to cause thermal effects within the tissue. Various electrosurgical surgical instruments and Ultrasonic surgical instruments have been developed for such purposes. In general, the delivery of energy to captured tissue can elevate the temperature of the tissue and, as a result, the energy can at least partially denature proteins within the tissue. Such proteins, like collagen, for example, can be denatured into a proteinaceous amalgam that intermixes and fuses, or seals, together as the proteins renature. As the treated region heals over time, this biological seal may be reabsorbed by the body's wound healing process.

Depending upon specific device configurations and operational parameters, ultrasonic surgical devices can provide substantially simultaneous transection of tissue and homeostasis by coagulation, desirably minimizing patient trauma. An ultrasonic surgical device may comprise a handpiece containing an ultrasonic transducer, and an instrument coupled to the ultrasonic transducer having a distally-mounted end effector (e.g., a blade tip) to cut and seal tissue. In some cases, the instrument may be permanently affixed to the handpiece. In other cases, the instrument may be detachable from the handpiece, as in the case of a disposable instrument or an instrument that is interchangeable between different handpieces. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Electrosurgical devices for applying electrical energy to tissue in order to treat and/or destroy the tissue are also finding increasingly widespread applications in surgical procedures. An electrosurgical device can be used in connection with a generator which may supply energy to the electrosurgical device. An electrosurgical device may comprise a handpiece and an instrument having a distally-mounted end effector (e.g., one or more electrodes). The end effector can be positioned against the tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical device may also comprise a cutting member that is movable relative to the tissue and the electrodes to transect the tissue.

The foregoing discussion is intended only to illustrate various aspects of the related art and should not be taken as a disavowal of claim scope.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 1 illustrates one embodiment of a surgical system comprising a generator and various surgical instruments usable therewith;

FIG. 2 illustrates one embodiment of an example ultrasonic device that may be used for transection and/or sealing;

FIG. 3 illustrates one embodiment of an end effector of the example ultrasonic device of FIG. 2.

FIG. 13 is an exemplary graph demonstrating an increasing trend in minimum cycle impedance;

FIG. 14 is an exemplary table format of a database;

FIG. 14A is an exemplary graph demonstrating power (P) supplied by the generator of FIG. 9A over treatment cycle time (T);

FIG. 15 illustrates a module for use with the system of FIG. 9A;

FIG. 15A illustrates a module for use with the system of FIG. 9A;

FIG. 16 illustrates a module for use with the system of FIG. 9A;

FIG. 17 illustrates a module for use with the system of FIG. 9A;

FIG. 18 illustrates a module for use with the system of FIG. 9A; and

DETAILED DESCRIPTION

Figure 4:
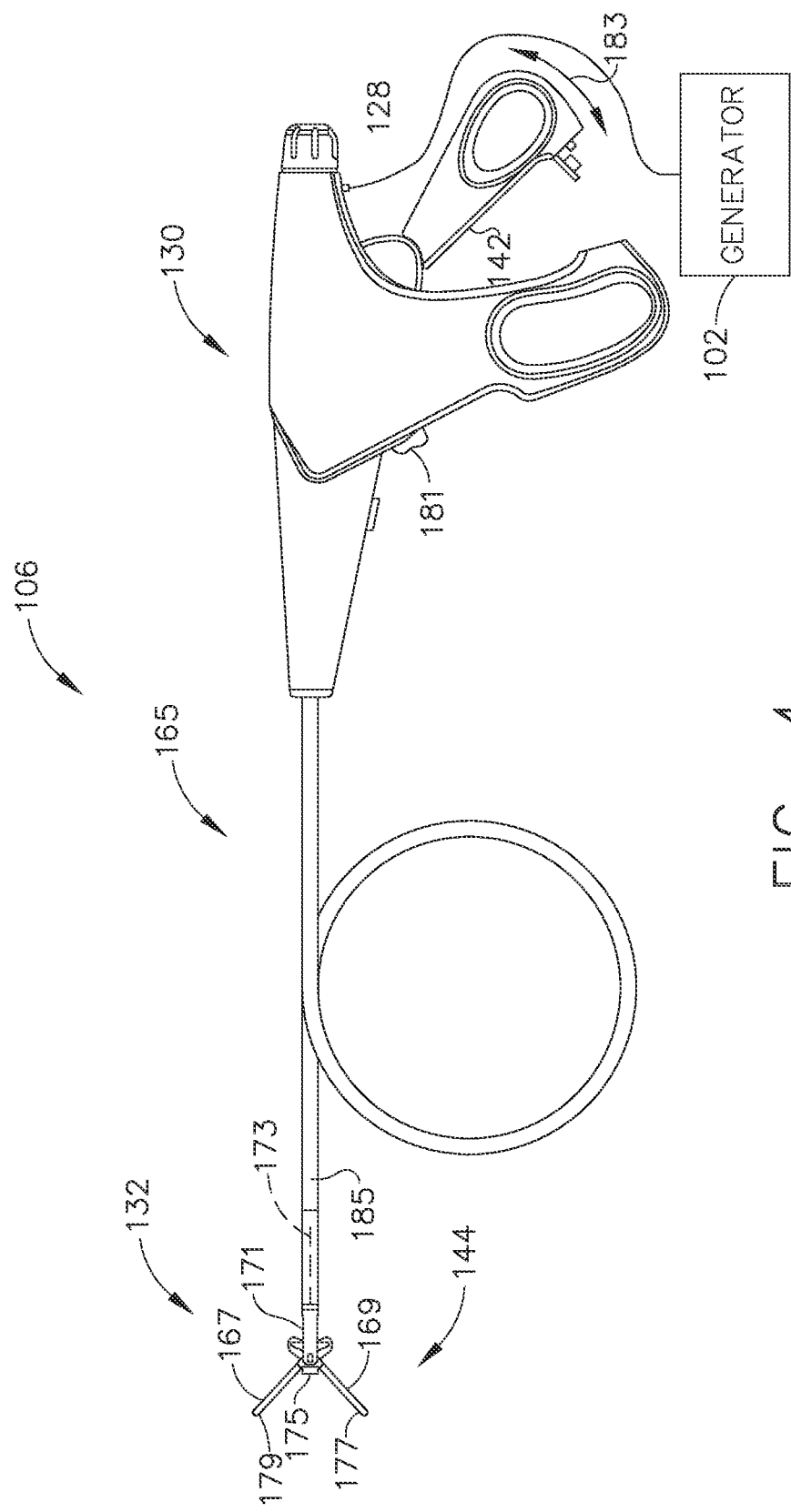
FIG. 4 illustrates one embodiment of an example electrosurgical device that may also be used for transection and sealing.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Various embodiments are directed to improved ultrasonic surgical devices, electrosurgical devices and generators for use therewith. Embodiments of the ultrasonic surgical devices can be configured for transecting and/or coagulating tissue during surgical procedures, for example. Embodiments of the electrosurgical devices can be configured for transecting, coagulating, scaling, welding, and/or desiccating tissue during surgical procedures, for example.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

Turning to the Drawings wherein like numerals denote like components throughout the several views, FIG. 1 illustrates and exemplary surgical system 100 comprising a generator 102 configurable for use with surgical devices. According to various embodiments, the generator 102 may be configurable for use with surgical devices of different types, including, for example, ultrasonic surgical device 104 and electrosurgical or RF surgical device 106. Although in the embodiment of FIG. 1 the generator 102 is shown separate from the surgical devices 104, 106, in certain embodiments the generator 102 may be formed integrally with either of the surgical devices 104, 106 to form a unitary surgical system. In certain instances, the generator/device combination can be powered by an internal power source such as, for example, a battery. Accordingly, the generator/device combination can be a cordless system that may not need to be connected to an external power source, for example.

FIG. 2 illustrates an example ultrasonic device 104 that may be used for transection and/or sealing. The device 104 may comprise a hand piece 116 which may, in turn, comprise an ultrasonic transducer 114. The transducer 114 may be in electrical communication with the generator 102, for example, via a cable 122 (e.g., a multi-conductor cable). The transducer 114 may comprise piezoceramic elements, or other elements or components suitable for converting the electrical energy of a drive signal into mechanical vibrations. When activated by the generator 102, the ultrasonic transducer 114 may cause longitudinal vibration. The vibration may be transmitted through an instrument portion 124 of the device 104 (e.g., via a waveguide embedded in an outer sheath) to an end effector 126 of the instrument portion 124. The generator 102 may be activated to provide the drive signal to the transducer 114 in any suitable manner. The specific drive signal configuration may be controlled based upon, for example, EEPROM settings in the generator 102 and/or user power level selection(s). See, for example, U.S. Patent Application Publication No. 2011/0087216 A1, entitled SURGICAL GENERATOR FOR ULTRASONIC AND ELECTROSURGICAL DEVICES, filed Oct. 1, 2010, the entire disclosure of which is hereby incorporated by reference herein.

FIG. 3 illustrates one embodiment of the end effector 126 of the example ultrasonic device 104. The end effector 126 may comprise a blade 151 that may be coupled to the ultrasonic transducer 114 via the wave guide (not shown). When driven by the transducer 114, the blade 151 may vibrate and, when brought into contact with tissue, may cut and/or coagulate the tissue, as described herein. According to various embodiments, and as illustrated in FIG. 3, the end effector 126 may also comprise a clamp arm 155 that may be configured for cooperative action with the blade 151 of the end effector 126. With the blade 151, the clamp arm 155 may comprise a set of jaws 140. The clamp arm 155 may be pivotally connected at a distal end of a shaft 153 of the instrument portion 124. The clamp arm 155 may include a clamp arm tissue pad 163, which may be formed from TEFLON® or other suitable low-friction material. The pad 163 may be mounted for cooperation with the blade 151, with pivotal movement of the clamp arm 155 positioning the clamp pad 163 in substantially parallel relationship to, and in contact with, the blade 151. By this construction, a tissue bite to be clamped may be grasped between the tissue pad 163 and the blade 151. The tissue pad 163 may be provided with a sawtooth-like configuration including a plurality of axially spaced, proximally extending gripping teeth 161 to enhance the gripping of tissue in cooperation with the blade 151. The clamp arm 155 may transition from the open position shown in FIG. 3 to a closed position (with the clamp arm 155 in contact with or proximity to the blade 151) in any suitable manner. For example, the hand piece 116 may comprise a jaw closure trigger 138. When actuated by a clinician, the jaw closure trigger 138 may pivot the clamp arm 155 in any suitable manner.

The end effector 126 may also comprise a pair of electrodes 159, 157. The electrodes 159, 157 may be in communication with the generator 102, for example, via the cable 122. The electrodes 159, 157 may be used, for example, to measure an impedance of a tissue bite present between the clamp arm 155 and the blade 151. The generator 102 may provide a signal (e.g., a non-therapeutic signal) to the electrodes 159, 157. As will be described in more detail below, the impedance of the tissue bite may be found, for example, by monitoring the current, voltage, etc. of the signal.

FIG. 4 illustrates one embodiment of an example electrosurgical device 106 that may also be used for transection and sealing. According to various embodiments, the transection and sealing device 106 may comprise a hand piece assembly 130, a shaft 165 and an end effector 132. The shaft 165 may be rigid (e.g., for laparoscopic and/or open surgical application) or flexible, as shown, (e.g., for endoscopic application). In various embodiments, the shaft 165 may comprise one or more articulation points. The end effector 132 may comprise jaws 144 having a first jaw member 167 and a second jaw member 169. The first jaw member 167 and second jaw member 169 may be connected to a clevis 171, which, in turn, may be coupled to the shaft 165. A translating member 173 may extend within the shaft 165 from the end effector 132 to the hand piece 130. At the hand piece 130, the shaft 165 may be directly or indirectly coupled to a jaw closure trigger 142 (FIG. 4).

The jaw members 167, 169 of the end effector 132 may comprise respective electrodes 177, 179. The electrodes 177, 179 may be connected to the generator 102 via electrical leads 187a, 187b (FIG. 5) extending from the end effector 132 through the shaft 165 and hand piece 130 and ultimately to the generator 102 (e.g., by a multiconductor cable 128). The generator 102 may provide a drive signal to the electrodes 177, 179 to bring about a therapeutic effect to tissue present within the jaw members 167, 169. The electrodes 177, 179 may comprise an active electrode and a return electrode, wherein the active electrode and the return electrode can be positioned against, or adjacent to, the tissue to be treated such that current can flow from the active electrode to the return electrode through the tissue. As illustrated in FIG. 4, the end effector 132 is shown with the jaw members 167, 169 in an open position. A reciprocating blade 175 is illustrated between the jaw members 167, 169.

Figure 5:
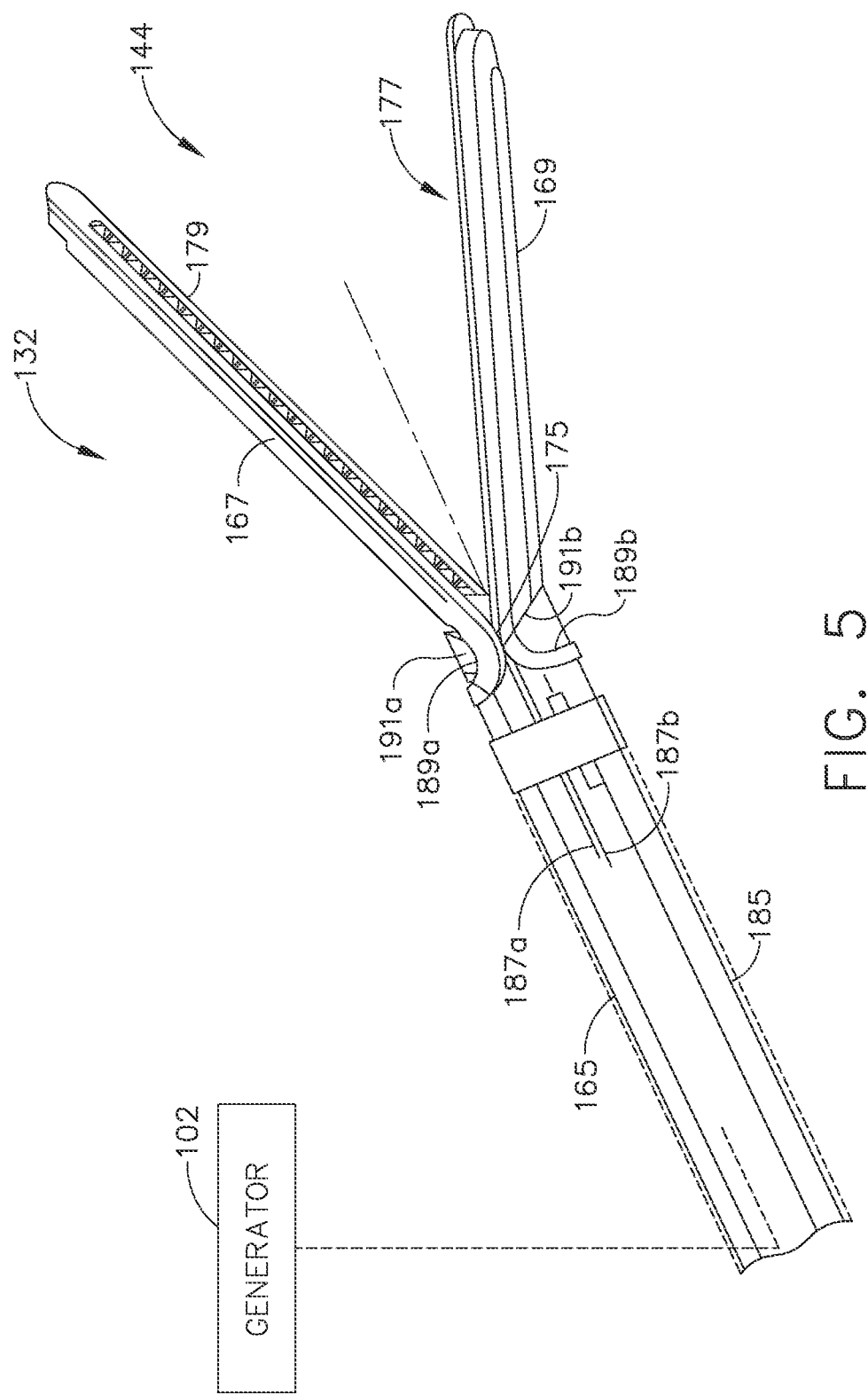
FIGS. 5, 6 and 7 illustrate one embodiment of the end effector shown in FIG. 4.
Figure 6:
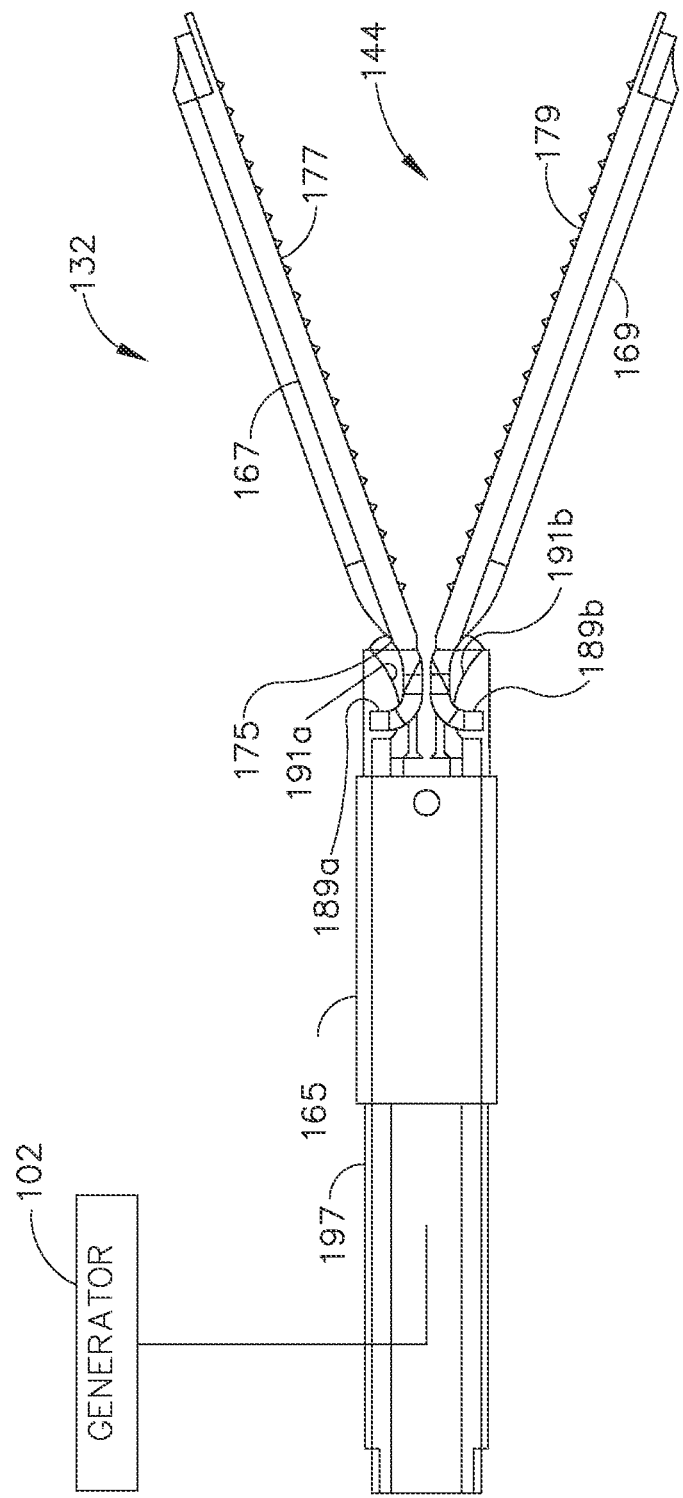
Figure 7:
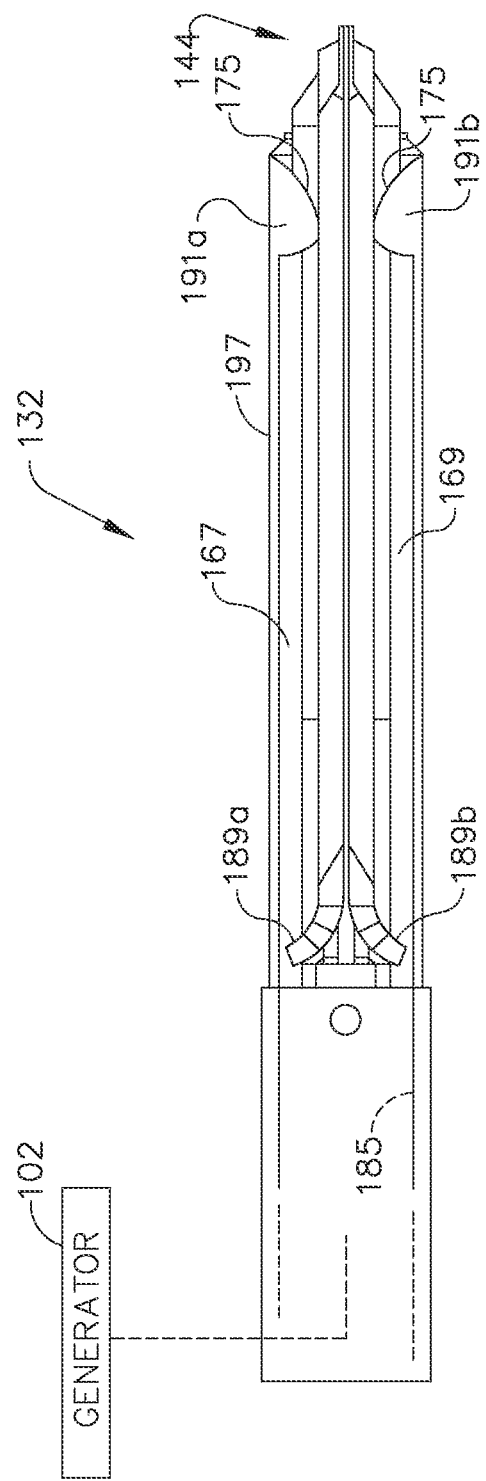

FIGS. 5, 6 and 7 illustrate one embodiment of the end effector 132 shown in FIG. 4. To close the jaws 144 of the end effector 132, a clinician may cause the jaw closure trigger 142 to pivot along arrow 183 from a first position to a second position. This may cause the jaws 144 to open and close according to any suitable method. For example, motion of the jaw closure trigger 142 may, in turn, cause the translating member 173 to translate within a bore 185 of the shaft 165. A distal portion of the translating member 173 may be coupled to a reciprocating member 197 such that distal and proximal motion of the translating member 173 causes corresponding distal and proximal motion of the reciprocating member. The reciprocating member 197 may have shoulder portions 191a, 191b, while the jaw members 167, 169 may have corresponding cam surfaces 189a, 189b. As the reciprocating member 197 is translated distally from the position shown in FIG. 6 to the position shown in FIG. 7, the shoulder portions 191a, 191b may contact the cam surfaces 189a, 189b, causing the jaw members 167, 169 to transition to the closed position. Also, in various embodiments, the blade 175 may be positioned at a distal end of the reciprocating member 197. As the reciprocating member extends to the fully distal position shown in FIG. 7, the blade 175 may be pushed through any tissue present between the jaw members 167, 169, in the process, severing it.

In use, a clinician may place the end effector 132 and close the jaws 144 around a tissue bite to be acted upon, for example, by pivoting the jaw closure trigger 142 along arrow 183 as described. Once the tissue bite is secure between the jaws 144, the clinician may initiate the provision of RF or other electro-surgical energy by the generator 102 and through the electrodes 177, 179. The provision of RF energy may be accomplished in any suitable way. See, for example, U.S. Patent Application Publication No. 2011/0087216 A1, entitled SURGICAL GENERATOR FOR ULTRASONIC AND ELECTROSURGICAL DEVICES, filed Oct. 1, 2010, the entire disclosure of which is hereby incorporated by reference herein.

The electrodes 177 and 179 may be used, for example, to measure impedance of a tissue bite present between the jaw members 167 and 169. The generator 102 may provide a signal (e.g., a non-therapeutic signal) to the electrodes 177 and 179. The impedance of the tissue bite may be found, for example, by monitoring the current, voltage, etc. of the signal. Alternatively, the jaw members 167 and 169 of the end effector 132 may comprise an additional pair of electrodes dedicated to measuring the impedance of a tissue bite present between the jaw members 167 and 169. The generator 102 may be in communication with such electrodes to provide the non-therapeutic signal.

Figure 8:
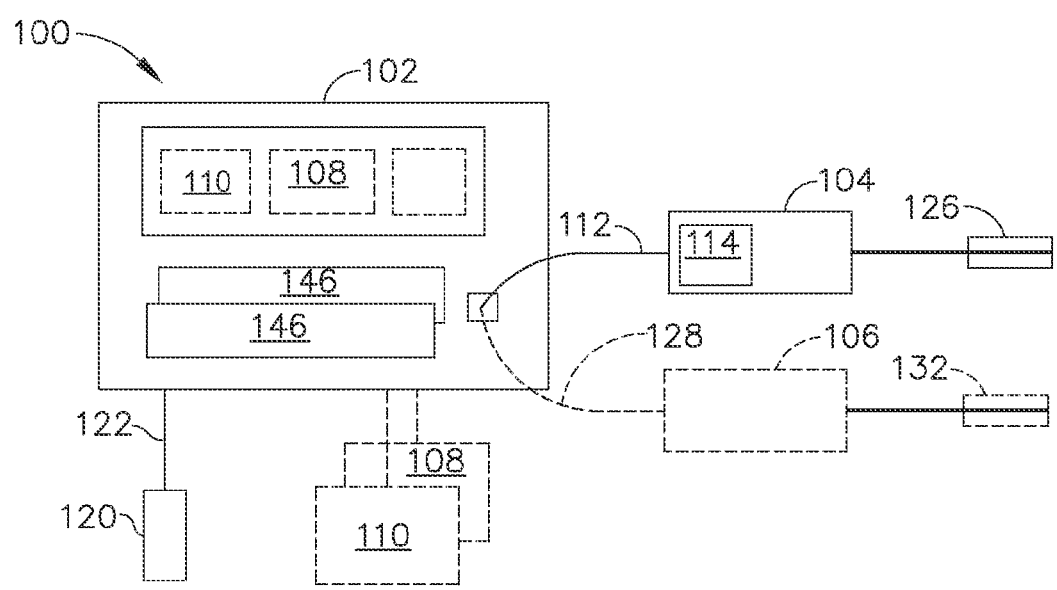
FIG. 8 is a diagram of the surgical system of FIG. 1.

FIG. 8 is a diagram of the surgical system 100 of FIG. 1. The generator 102 may comprise several separate functional elements, such as modules and/or blocks. Different functional elements or modules may be configured for driving the different kinds of surgical devices 104, 106. For example an ultrasonic generator module 108 may drive an ultrasonic device, such as the ultrasonic device 104. An electrosurgery/RF generator module 110 may drive the electrosurgical device 106. For example, the respective modules 108, 110 may generate respective drive signals for driving the surgical devices 104, 106. In various embodiments, the ultrasonic generator module 108 and/or the electrosurgery/RF generator module 110 each may be formed integrally with the generator 102. Alternatively, one or more of the modules 108, 110 may be provided as a separate circuit module electrically coupled to the generator 102. (The modules 108 and 110 are shown in phantom to illustrate this option.) Also, in some embodiments, the electrosurgery/RF generator module 110 may be formed integrally with the ultrasonic generator module 108, or vice versa. See, for example, U.S. Patent Application Publication No. 2011/0087216 A1, entitled SURGICAL GENERATOR FOR ULTRASONIC AND ELECTROSURGICAL DEVICES, filed Oct. 1, 2010, the entire disclosure of which is hereby incorporated by reference herein. In certain instances, the surgical system 100 may comprise one or more modules which can be employed with multiple surgical instruments. For example, a module can be employed with an ultrasonic device, such as the ultrasonic device 104 and can be employed with an electrosurgical device such as, for example, the electrosurgical device 106; in such instance, the module can be employed to generate drive signals for driving the surgical devices 104 and 106, for example.

In certain instances, the generator 102 may comprise an input device 145 (FIG. 1) located, for example, on a front panel of the generator 102 console. The input device 145 may comprise any suitable device that generates signals suitable for programming the operation of the generator 102. In operation, the user can program or otherwise control operation of the generator 102 using the input device 145. The input device 145 may comprise any suitable device that generates signals that can be used by the generator (e.g., by one or more processors contained in the generator) to control the operation of the generator 102 (e.g., operation of the ultrasonic generator module 108 and/or electrosurgery/RF generator module 110).

In various embodiments, the input device 145 includes one or more of buttons, switches, thumbwheels, keyboard, keypad, touch screen monitor, pointing device, remote connection to a general purpose or dedicated computer. In other embodiments, the input device 145 may comprise a suitable user interface, such as one or more user interface screens displayed on a touch screen monitor, for example. Accordingly, by way of the input device 145, the user can set or program various operational parameters of the generator, such as, for example, current (I), voltage (V), frequency (f), impedance (Z), and/or period (T) of a drive signal or signals generated by the ultrasonic generator module 108 and/or electrosurgery/RF generator module 110.

The generator 102 may also comprise an output device 147 (FIG. 1) located, for example, on a front panel of the generator 102 console. The output device 147 includes one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators).

Figure 9:
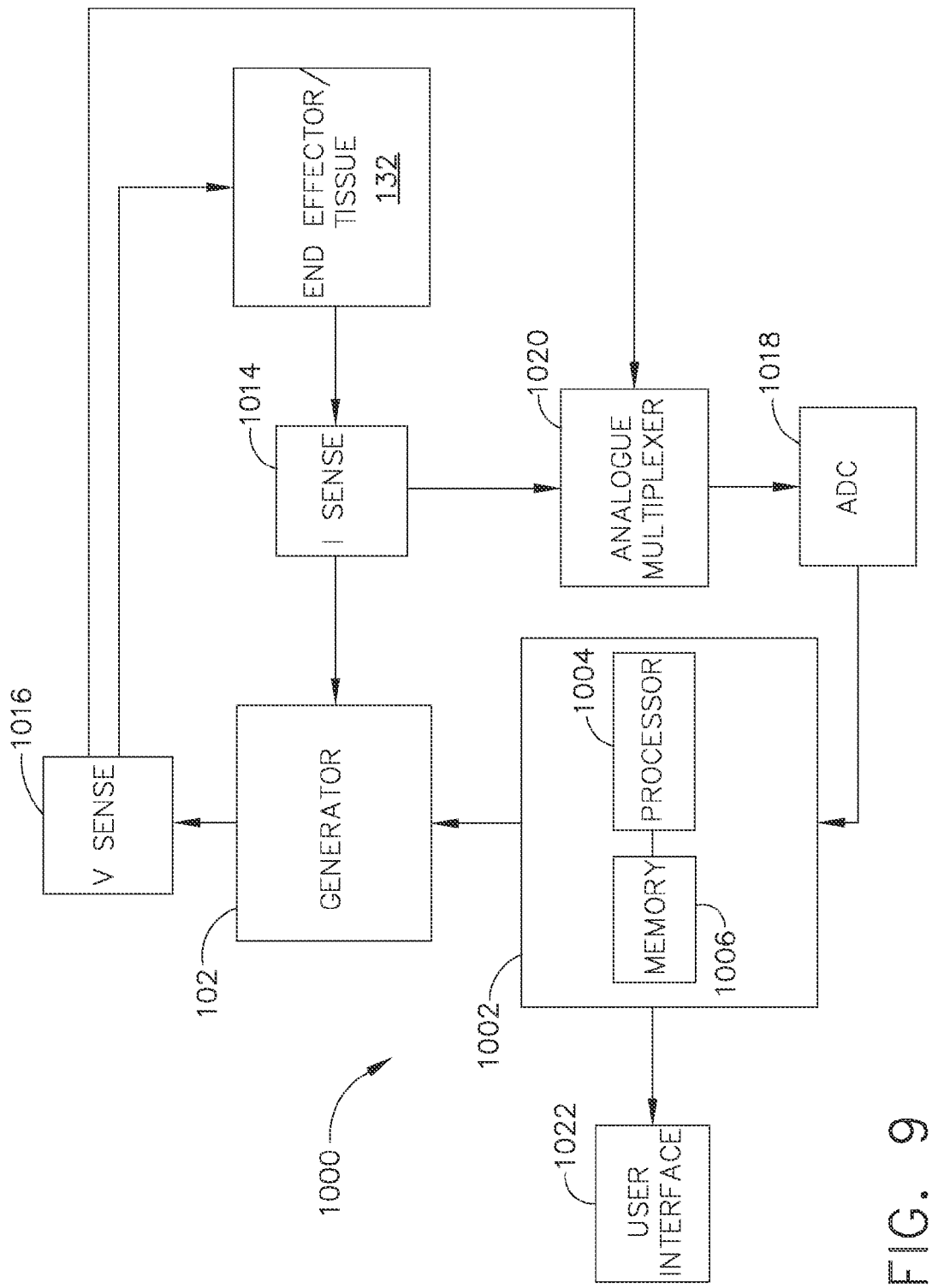
FIG. 9 illustrates a block diagram of a surgical system comprising a generator and a controller in accordance with certain embodiments described herein.

FIG. 9, illustrates an exemplary system 1000 for use with various surgical instruments of the surgical system 100 such as, for example, the ultrasonic device 104 and/or the RF surgical device 106. The system 1000 may include a controller 1002 which may comprise a processor 1004 and a memory 1006. It should be recognized that the system 1000 may comprise multiple processors 1004 and/or multiple memory units 1006. The memory 1006 may store a number of software modules such as, for examples, one or more of the modules shown in FIGS. 10-12 and 15-18. Although certain modules and/or blocks of the system 1000 may be described by way of example, it can be appreciated that a greater or lesser number of modules and/or blocks may be used. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), field programmable gate arrays (FPGAs), Application Specific Integrated Circuits (ASICs), Radio-frequency identifiers (RFIDs), circuits, registers and/or software components, e.g., programs, subroutines, logic and/or combinations of hardware and software components. For example, modules such as module 1008 (See FIG. 10) may comprise software code that may be executed by the processor 1004, which may cause the processor 1004 to perform various actions dictated by the software code of the various modules, as explained further below.

One or more of the modules described in FIGS. 10-12 and 15-18 may comprise one or more embedded applications implemented as firmware, software, hardware, or any combination thereof. One or more of the modules 1008-1010 and 1502, 1504, 1506, and 1508 may comprise various executable modules such as software, programs, data, drivers, application program interfaces (APIs), and so forth. The firmware may be stored in the memory 1006 which may comprise a nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM). In certain instances, the memory 1006 can be integrated with or fixed to the generator 102, for example. In certain instances, the memory 1006 can be integrated with or fixed to a surgical device such as, for example, the ultrasonic device 104 and/or the RF surgical device 106. Alternatively, in certain instances, the memory 1006 can be removably coupled to the generator 102 or the surgical device, for example. In certain instances, data stored on the memory 1006 can be accessed through an access port such as, for example, a Universal Serial Bus (USB). In certain instances, the memory 1006 can be separated or removed from the generator 102 or the surgical device to access the stored data, for example. In certain instances, the memory 1006 could be stored in a separate compartment positioned on top of the generator 102, for example. In certain instances, the data stored on the memory 1006 can be accessible wirelessly. In certain instances, for example, the data stored on the memory 1006 can be accessible via one or more wireless communication protocols such as, for example, IEEE 802.15.4 (ZigBee), IEEE 802.11a, IEEE 802.11b, IEEE 802.11g, IEEE 802.11n, IEEE 802.16a, IEEE 802.16g, Bluetooth or Infrared wireless communication protocols.

Referring primarily to FIGS. 3, 4, and 9, the system 1000 can be adapted for monitoring accumulation of biological material onto an end effector of a surgical instrument used to treat tissue. In certain instances, the system 1000 can be configured to identify and store data concerning incidents of biological material accumulation that can interfere with normal operation of the surgical instrument. In certain instances, the system 1000 may be configured to alert a user to incidents of biological material accumulation that can interfere with normal operation of the surgical instrument. Biological material may accumulate onto an end effector such as, for example, the end effector 126 and/or the end effector 132 during repetitive use in tissue treatment cycles. The heat generated by the ultrasonic device 104 and/or the RF surgical device 106 may, in part, cause biological material such as, for example, denatured proteins and/or coagulated blood to adhere to the blade 151 and/or the clamp arm 155 of the ultrasonic device 104 and/or one or both of the jaw members 167 and 169 of the RF surgical device 106, for example. Excessive accumulation of biological material may interfere with the normal operation of the ultrasonic device 104 and/or the RF surgical device 106. For example, the accumulating biological material may increase energy requirements during a treatment cycle.

In certain instances, the system 1000 can be configured to monitor biological material accumulation onto the jaw members 167 and 169 by monitoring a distance between the jaw members 167 and 169, for example. In certain instances, the jaw members 167 and 169 may define a gap therebetween in the closed configuration; the gap may increase in size in response to accumulation of biological material onto one or both of the jaw members 167 and 169. In other words, the size of the gap between the jaw members 167 and 169, in the closed configuration, may correspond to the amount of biological material accumulated onto the jaw members 167 and 169, for example. In certain instances, the size of the gap between the jaw members 167 and 169, in the closed configuration, may be directly proportional to the amount of biological material accumulated onto the jaw members 167 and 169, for example. In certain instances, the distance between the jaw members 167 and 169 can be monitored over time and stored in the memory 1006. In certain instances, the system 1000 may comprise one or more position sensors for monitoring the distance between the jaw members 167 and 169 in the closed configuration. In certain instances, the system 1000 can be configured to alert a user if the gap size exceeds a predetermined threshold, for example.

In certain instances, the system 1000 may comprise a load cell (not shown) which can be operably coupled to a cutting member employed to cut tissue captured between the jaw member 167 and 169. The load cell may be configured to sense tissue resistance to the cutting member. Said another way, the load cell can be configured to sense the force required to advance the cutting member through the captured tissue. In certain instances, the measured force can be progressively higher than expected due to biological material accumulation onto the jaw members 167 and 169. In certain instances, the system 1000 may monitor the force required to advance the cutting member and detect if the force exceeds a threshold, for example. In certain instances, the system 1000 can be configured to alert a user if the force exceeds the threshold. In certain instances, the cutting member can be operably coupled to a motor that can generate rotational motions to advance the cutting member against the captured tissue; and a motor driver can control the motor. Furthermore, the system 1000 can be in signal communication with the motor driver. As the motor advances the cutting member, the system 1000 can determine the current drawn by the motor, for example. In such instances, the force required to advance the cutting member can correspond to the current drawn by the motor, for example. As described above, the force can be progressively higher than expected due to biological material accumulation onto the jaw members 167 and 169; and accordingly, the current drawn by the motor may be progressively higher than expected as well. In certain instances, if the increase in the current drawn by the motor exceeds a predefined threshold, the system 1000 may conclude that biological material accumulation onto the jaw members 167 and 169 is excessive and, in response, may alert the user. The reader will appreciate that, among other things, motor speed, power, and/or voltage can be monitored to evaluate the resistance force experienced by the cutting member as the cutting member is advanced against tissue, for example.

In certain instances, the jaw members 167 and 169 may be transitioned between a first (open) position and a second (closed) position by a slidable blade member (not shown) which may comprise an "I"-beam type cross-section. The slidable blade member may serve two functions: (i) to transect the captured tissue, and (ii) to transition the jaw members 167 and 169 between the open position and the closed position. Exemplary closure mechanisms suitable for use with the present disclosure are described in U.S. Pat. No. 6,500,176, entitled ELECTROSURGICAL SYSTEMS AND TECHNIQUES FOR SEALING TISSUE, and filed Oct. 23, 2000, which is hereby incorporated by reference herein in its entirety. In addition, U.S. Pat. No. 7,189,233, entitled ELECTROSURGICAL INSTRUMENT, and filed Sep. 3, 2004, is hereby incorporated by reference herein in its entirety.

In certain instances, the slidable blade member may comprise flanges that are configured to engage the jaw members 167 and 169, for example. In addition, the slidable blade member may be operably coupled to a motor that can generate rotational motions to advance and retract the slidable blade member to transition the jaw members 167 and 169 between the open position and the closed position. In certain instances, the system 1000 may comprise a load cell (not shown) which can be coupled to the slidable blade member. The load cell may be configured to sense the force required to retract the slidable blade member at predetermined positions along the path of the slidable blade member. The reader will appreciate that biological material accumulation onto one or both of the jaw members 167 and 169 may cause jaw members to adhere together and resist the opening forces applied by the slidable blade member during the retraction of the slidable blade member. In certain instances, the greater the biological material accumulation, the greater the force required to separate the jaw members 167 and 169. In certain instances, the force required to separate the jaw members 167 and 169 can be progressively higher than expected due to biological material accumulation onto the jaw members 167 and 169. In certain instances, the system 1000 may monitor the force required to separate the jaw member 167 and 169 and detect if the force exceeds a threshold, for example. In certain instances, the system 1000 can be configured to alert a user if the force exceeds the threshold.

Further to the above, the system 1000 can be configured to monitor biological material accumulation onto the first jaw member 167 and/or the second jaw member 169 of the surgical device 106 by monitoring impedance (Z) between the electrodes 177 and 179 of the surgical device 106, for example. Further, the system 1000 can be configured, in a similar manner, to monitor biological material accumulation onto the blade 151 and/or the clamp arm 155 of the surgical device 104 by monitoring impedance (Z) between the electrodes 157 and 159, for example. The reader will appreciate that some of the components of the system 1000 can be integrated with the generator 102. In certain circumstances, some of the components of the system 1000 can be integrated with the hand piece 116 of the ultrasonic device 104 or the hand piece 130 of the RF surgical device 106. For illustration purposes, the following disclosure describes the operation of the system 1000 with the electrodes 177 and 179 of the surgical device 106. The reader will appreciate that the system 1000 can also be employed, in a similar manner, with electrodes 157 and 159 of the surgical device 104.

Further to the above, the system 1000 may monitor the biological material accumulation by monitoring impedance Z of tissue grasped between the jaw members 167 and 169. The system 1000 can be configured to measure the impedance Z in a similar manner to that described in U.S. Patent Application Publication No. 2011/0087216 A1, entitled SURGICAL GENERATOR FOR ULTRASONIC AND ELECTROSURGICAL DEVICES, filed Oct. 1, 2010, the entire disclosure of which is hereby incorporated by reference herein. For example, the processor 1004 can be configured to employ the generator 102 to apply a non-therapeutic radio frequency (RF) signal to tissue grasped by the end effector 132 between the jaw members 167 and 169. In certain instances, a current sense circuit 1014 can be employed to sense current flowing between electrodes 177 and 179 through the tissue. Furthermore, a voltage sense circuit 1016 can be employed to sense an output voltage applied to the electrodes 177 and 179 by the generator 102. The sensed values of current and voltage may be applied to an analog-to-digital converter (ADC) 1018 via an analog multiplexer 1020 circuit or switching circuit arrangement. The analog multiplexer 1020 may transmit the appropriate analog signal to the ADC 1018 for conversion. The processor 1004 may be configured to receive the digital output of the ADC 1018 and calculate the impedance Z of the tissue based on the measured values of current and voltage. It is worthwhile noting that the RF energy applied to the tissue for purposes of measuring the tissue impedance Z can be a low level non-therapeutic signal that may not contribute in a significant manner, or at all, to the treatment of the tissue.

Figure 10:
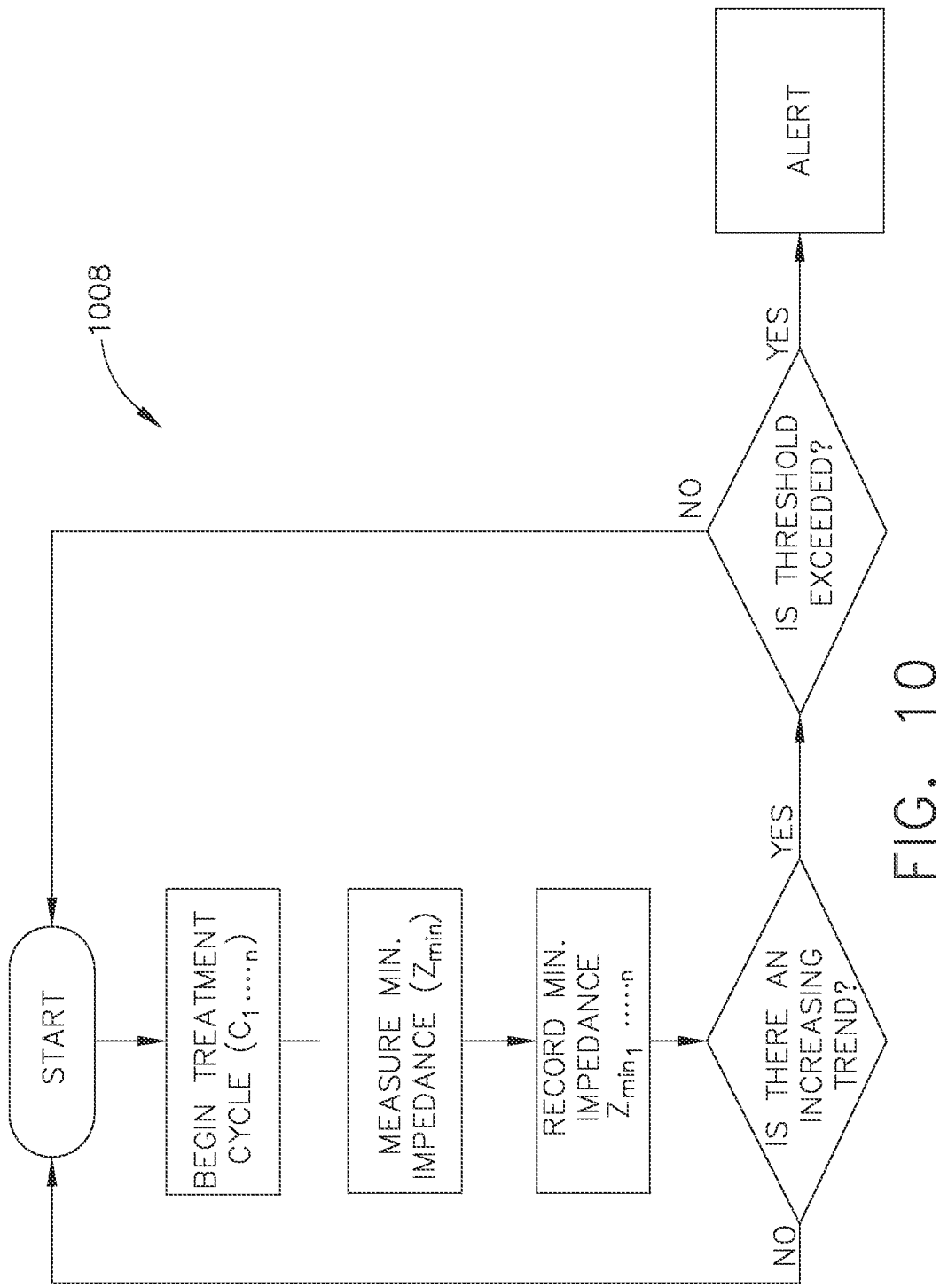
FIG. 10 illustrates a module for use with the system of FIG. 9.

Referring to FIGS. 9, 10, and 13, the system 1000 may comprise a module such as, for example, the module 1008 which can be configured to monitor biological material accumulation onto the jaw members 167 and 169 during multiple treatment cycles by monitoring minimum tissue impedance Zmin recorded during each of a plurality of treatment cycles. An increasing trend in the recorded minimum tissue impedance Zmin, as illustrated in FIG. 13, can indicate biological material accumulation onto the jaw members 167 and 169. In certain instances, the module 1008 can be configured to alert a user to clean the jaw members 167 and 168, for example, if the recorded minimum tissue impedance Zmin exceeds a predetermined threshold reflecting an excessive accumulation of biological material, as illustrated in FIG. 13.

The reader will appreciate that tissue impedance increases, at least initially, during a treatment cycle. In one non-limiting theory, the increase noted in tissue impedance can be explained by water evaporation resulting from the heat generated during tissue treatment. In other words, as tissue is treated water stored in the tissue may evaporate causing the treated tissue to become less conductive to electricity which, in turn, yields higher tissue impedance. As such, the biological material accumulating during use on the jaw members 167 and 169 may comprise a relatively high tissue impedance Z due to heat exposure during previous treatment cycles, for example. As the jaw members 167 and 168 grasp new tissue and as a new treatment cycle is activated, more biological material may accumulate causing the current passing between the electrodes 177 and 179 to experience higher minimum impedance at the onset of the new treatment cycle. The processor 1004 (FIG. 9) can be configured to detect the increase in the minimum tissue impedance Zmin by monitoring and recording, in the memory 1006, a value for the minimum tissue impedance $Zmin_{(1 \ldots n)}$ at the onset of each of a number of treatment cycles $C_{(1 \ldots n)}$. An increasing trend in the recorded minimum tissue impedance Zmin may indicate biological material accumulation.

In certain instances, the processor 1004 can be configured to alert a user of the surgical device 106 to clean the jaw members 167 and 168 if the recorded minimum tissue impedance (Zmin) exceeds a predetermined threshold, as illustrated in FIG. 13. For example, the system 1000 may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). The processor 1004 can be configured to alert the user of the surgical device 106 to clean the jaw members 167 and 168 through such devices.

Figure 11:
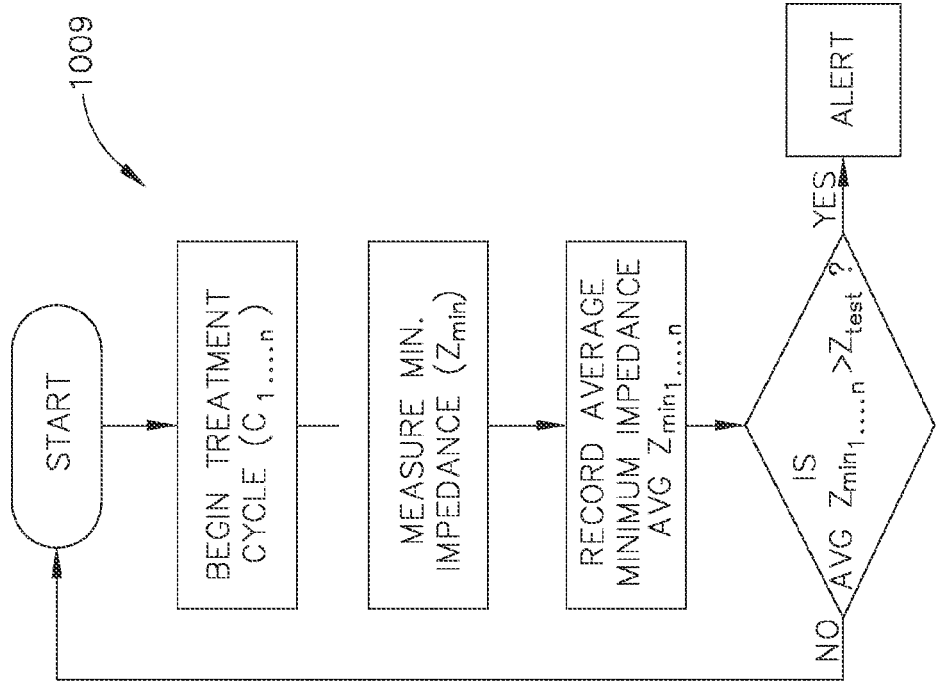
FIG. 11 illustrates a module for use with the system of FIG. 9.

Referring now to FIG. 11, another module 1009 can be employed with the surgical system 1000 to monitor biological material accumulation and alert a user if the accumulation reaches a predetermined threshold. As previously discussed, the processor 1004 can be configured to monitor tissue impedance and measure a value for the minimum tissue impedance $Zmin_{(1 \ldots n)}$ at the onset of each of a number of treatment cycles $C_{(1 \ldots n)}$. Furthermore, the processor 1004 can be configured to store, in the memory 1006, the average of the measured values of the minimum tissue impedance AVG $Zmin_{(1 \ldots n)}$ and compare the stored average to a prerecorded tissue impedance Ztest. The processor 1004 can be programmed to alert a user, as previously discussed, to clean the jaw members 167 and 169 if the AVG $Zmin_{(1 \ldots n)}$ exceeds Ztest. In certain instances, the processor 1004 can be programmed to alert a user to clean the jaw members 167 and 169 if the AVG $Zmin_{(1 \ldots n)}$ exceeds Ztest beyond a predetermined tolerance.

In certain circumstances, the processor 1004 can be programmed to alert the user to clean the jaw members 167 and 169 if the AVG $Zmin_{(1 \ldots n)}$ exceeds Ztest by approximately 10%, by approximately 20%, by approximately 30%, by approximately 40%, by approximately 50%, by approximately 60%, by approximately 70%, by approximately 80%, by approximately 90%, and/or by approximately 100%, for example. In certain circumstances, the processor 1004 can be programmed to issue a plurality of alerts. For example, a first alert can be issued when the AVG $Zmin_{(1 \ldots n)}$ exceeds Ztest by approximately 50% and a second alert at approximately 200%

Figure 12:
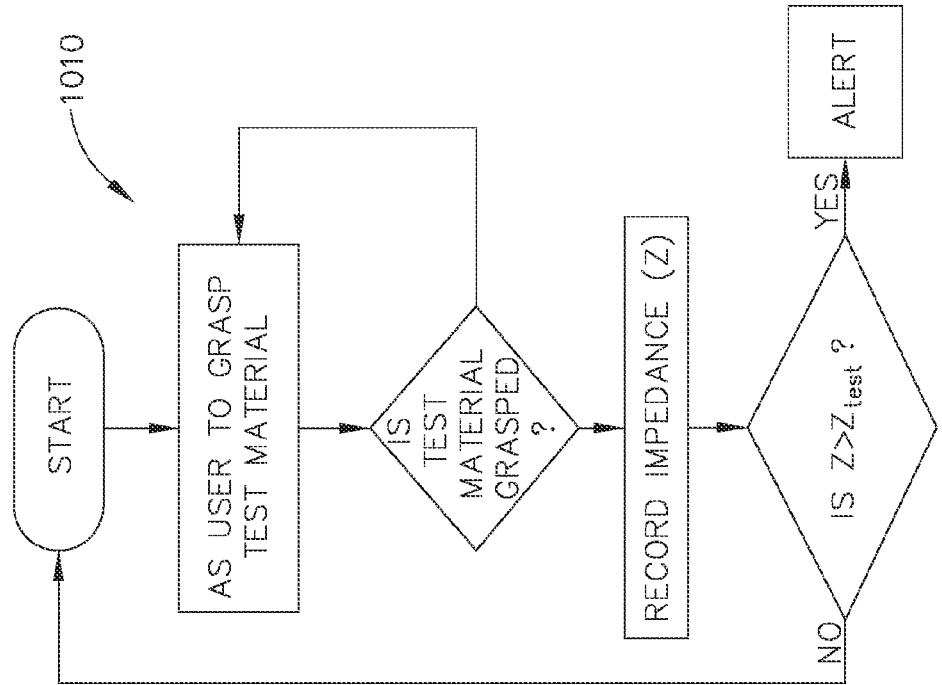
FIG. 12 illustrates a module for use with the system of FIG. 9.

Referring now to FIG. 12, yet another module 1010 can be employed with the system 1000 to monitor biological material accumulation and alert a user if the accumulation exceeds a threshold determined by impedance of a test material. The processor 1004 can be configured to prompt a user to measure the test material's impedance Z and compare it to a stored value Ztest for the impedance of the test material. The processor 1004 can be configured to prompt the user, as previously discussed, to clean the jaw members 167 and 169 if the measured test material's impedance Z exceeds Ztest by an acceptable tolerance. For example, the processor 1004 can be programmed to alert the user if the impedance Z and the stored value Ztest for the impedance of the test material differ by approximately 10%, by approximately 20%, by approximately 30%, by approximately 40%, by approximately 50%, by approximately 60%, by approximately 70%, by approximately 80%, by approximately 90%, and/or by approximately 100%, for example. In certain circumstances, the processor 1004 can be programmed to issue a plurality of alerts. For example, a first alert can be issued at approximately 50% and a second alert at approximately 200%.

In certain circumstances, the processor 1004 can be configured to prompt the user to record and store a Ztest value for the impedance of the test material while the jaw members 167 and 169 are clean such as, for example, at the onset of the surgical procedure. In such circumstances, the processor 1004 may prompt the user to grasp the test material between the jaw members 167 and 169. Upon receiving confirmation that the test material is grasped between the jaw members 167 and 169, the processor 1004 may record a test impedance value Ztest of the test material and may store the recorded value in the memory 1006, for example. The processor 1004 may then prompt the user, following a predetermined number of treatment cycles for example, to assess the biological material accumulation onto the jaw members 167 and 169 by measuring the impedance Z of the test material. If the measured value of the test material impedance Z exceeds the stored Ztest value, the processor 1004 may prompt the user to clean the jaw members 167 and 169. In certain circumstances, the test material can be provided with the surgical device 106 in a kit, for example. Alternatively, the test material can be a material readily available in a surgical environment such as, for example, surgical gauze.

Referring again to FIG. 9, the present disclosure further provides a method for using the system 1000 to alert a user to excessive biological material accumulation onto an end effector of a surgical instrument used to treat tissue such as for example, the surgical device 106. The method includes providing a non-therapeutic signal across the jaw members 167 and 169 of the surgical device 106, detecting impedance between the electrodes 177 and 179 in response to the non-therapeutic signal, comparing detected impedance to a predetermined threshold impedance, and providing a signal when the detected impedance exceeds the predetermined threshold impedance such as, for example, an alert signal to a user of the surgical device 106, as previously described.

Referring Primarily to FIGS. 3, 4, 9A, and 14 the system 1000 can be configured to compile values of a plurality of operational parameters of the surgical system 100. For example, in certain instances, the system 1000 can be configured to compile values of a plurality of operational parameters of a surgical instrument of the surgical system 100 such as, for example, the ultrasonic device 104 and/or the RF surgical device 106, during a plurality of tissue treatment cycles performed using the surgical instrument. For example, the processor 1004 can be configured to receive and/or calculate the values of the plurality of operational parameters during each of the plurality of treatment cycles and store such values in the memory 1006. In certain circumstances, the stored values can be organized into a database such as, for example, a database 1500 (See FIG. 14). In certain instances, in certain instances, the system 1000 can be configured to compile values of a plurality of operational parameters of a generator of the surgical system 100 such as, for example, the generator 102.

Figure 9A:
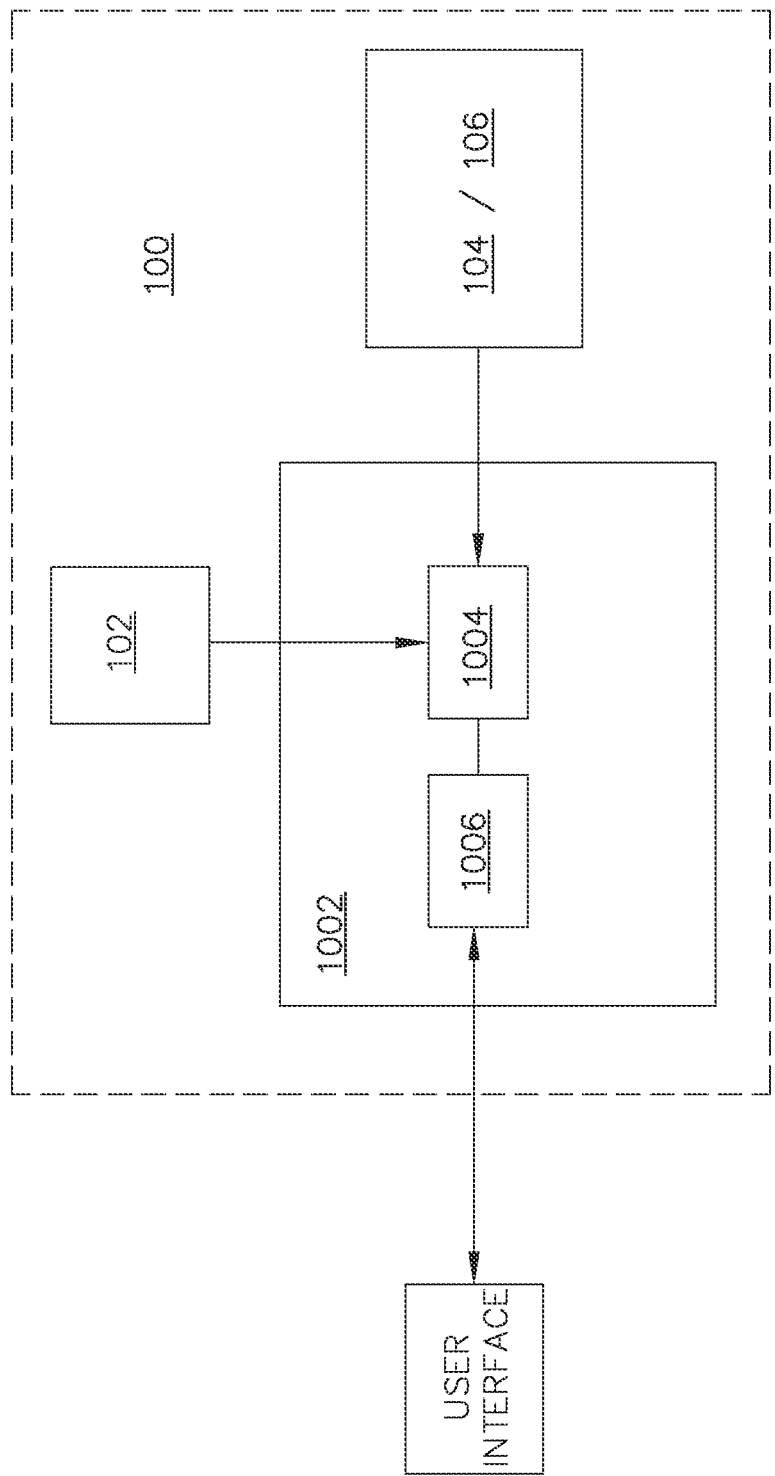
FIG. 9A illustrates a block diagram of a surgical system comprising a generator and a controller in accordance with certain embodiments described herein.

Referring Primarily to FIGS. 3, 4, and 9A, a tissue treatment cycle may comprise one or more therapeutic drive signals which can be generated by the generator 102, for example, and delivered to the tissue using the ultrasonic device 104 or the RF surgical device 106. See, for example, U.S. Patent Application Publication No. 2011/0087216 A1, entitled SURGICAL GENERATOR FOR ULTRASONIC AND ELECTROSURGICAL DEVICES, filed Oct. 1, 2010, the entire disclosure of which is hereby incorporated by reference herein. The system 1000 can also be configured to monitor and store the values of some or all of the operational parameters of the generator 102 in connection with one or more of the treatment cycle delivered by the generator 102 to the tissue. These operational parameters may include, for example, current (I), voltage (V), frequency (f), peak power (PP), energy expenditure (E), tissue impedance (Z), duty cycle (DT), end effector temperature, and/or time period (T) of a drive signal or signals during one or more tissue treatment cycles delivered by the generator 102. In certain instances, the system 1000 can be configured to track other operational parameters and usage data such as, for example, total surgical procedure time, tissue type, surgical procedure type, user information, hospital information, physician information, procedure location, error codes, device identification information including, for example, serial number and/or device lot, and/or total time of operation. The reader will appreciate that the listed operational parameters are meant to be illustrative rather than exhaustive and that other operational parameters of the generator 102, the surgical procedure, the ultrasonic device 104, and/or the RF surgical device 106 can also be monitored and stored by the system 1000 during one or more treatment cycles. In certain instances, the surgical system 100 may comprise one or more motors which can generate rotational forces for powering various drive assemblies such as, for example, a cutting member drive assembly adapted for advancement and retraction of a cutting member, for example. In such instances, the system 1000 can also be configured to track various operational parameters in connection with the motor such as, for example, motor temperature, motor voltage, motor current, motor rpm, motor cycles, and/or force on the motor's drivetrain, for example.

Further to the above, the processor 1004 can be configured to monitor and store, in the memory 1006, the number of times a surgical instrument of the surgical system 100 such as, for example, the ultrasonic device 104, and/or the RF surgical device 106 is coupled to the generator 102. In certain instances, the processor 1004 can be configured to monitor and store, in the memory 1006, the number of times various end effectors are employed and the frequency of utilization of each of the employed end effectors.

For example, a sensor can be operably coupled to the processor 1004 and can be configured to detect coupling engagement of the surgical instrument to the generator 102. In at least one example, a circuit can be operably coupled to the processor 1004 and may comprise a switch that can be transitionable between an open configuration while the surgical instrument is not connected to the generator 102 and a closed configuration while the surgical instrument is connected to the generator 102. In such circumstances, the switch may close the circuit upon connecting the surgical instrument to the generator 102. In response, the circuit may transmit a signal to alert the processor 1004 to increase by one a count stored in the memory 1006 of the number of times the surgical instrument is connected to the generator 102, for example.

Referring to FIG. 14, illustrated is an exemplary table form of the database 1500. The system 1000 can be configured to gather and store the values of the various operational parameters and other usage data in the memory 1006 in the database 1500, for example. The reader will appreciate that the values of the various operational parameters can be stored in the memory 1006 in a variety of different arrangements and that the database 1500 is an exemplary illustrative technique for arranging data stored in the memory 1006. As illustrated in FIG. 14, the first column may list treatment cycle identification numbers. Other columns may be dedicated, for example, to current (I), voltage (V), peak power (PP), energy expenditure (E), tissue impedance (Z), cycle time (T), end effector temperature, tissue type, procedure type, procedure time, operation time, and user information, hospital information, procedure location. The processor 1004 can be configured to store the values of the operational parameters compiled during a treatment Cycle C1, for example, in the row dedicated to the treatment cycle C1. Other arrangements for the database 1500 are contemplated by the present disclosure.

In certain instances, as described above, the one or more of the electrosurgical instruments of the present disclosure can be utilized with a motor which can generate rotational forces for powering various drive assemblies such as, for example, a cutting member drive assembly for advancement and retraction of a cutting member. In such instances, the processor 1004 can be configured to store, in the database 1500, values of various operational parameters in connection with the motor such as, for example, motor temperature, motor voltage, motor current, motor rpm, motor cycles, and/or force on the motor's drivetrain, for example.

As described elsewhere in greater detail, a treatment cycle may involve passing one or more therapeutic drive signals generated by the generator 102 through tissue. FIG. 15 illustrates an exemplary module 1502 for use by the processor 1004 for gathering and storing the values of the operational parameters and other usage data during a plurality of treatment cycles in the database 1500, for example. In certain circumstances, the processor 1004 can be configured to calculate cycle time (T) from beginning to termination of a therapeutic drive signal delivered to tissue. Calculated cycle time (T) can be stored in a dedicated Column in the database 1500, as illustrated in FIG. 14. Furthermore, the current sense circuit 1014 can be employed by the processor 1004 to sense current passing through the tissue during the treatment cycle. Furthermore, the voltage sense circuit 1016 can be employed by the processor 1004 to sense output voltage applied by the generator 102 during the treatment cycle. The sensed values of current and voltage can be communicated to the processor 1004, as previously described. The processor 1004 may calculate an average value for the voltage V1 and current I1 monitored during the treatment cycle which can be stored in dedicated columns in the database 1500, as illustrated in FIG. 14.

Further to the above, the processor 1004 can be configured to monitor active time periods, while energy is being applied to tissue, and inactive time periods, while energy is not being applied to the tissue. In certain instances, the ratios of the active time periods to the corresponding inactive time periods can be stored in the memory 1006. In certain instances, the processor 1004 may calculate average tissue impedance (Z) and minimum tissue impedance (Zmin) during the treatment cycle from the sensed values of voltage and current. The average tissue impedance (Z) and the minimum tissue impedance (Zmin) values can then be stored in dedicated columns in the database 1500, as illustrated in FIG. 14. In certain circumstances, the processor 1004 can be configured to store a plurality of values of each operating parameter during a plurality of time periods during a treatment cycle. In such circumstances, each treatment cycle may be represented by a dedicated table, for example.

Further to the above, the processor 1004 can be configured to calculate total energy (E) delivered to tissue during the treatment cycle. For example, the processor 1004 may monitor the cycle time (T) and the power delivered to tissue over that time as calculated from the sensed voltage and current values. The total energy (E) may then be determined by calculating the total area under the Power (P) vs. Cycle time (T) curve, as illustrated in FIG. 14A. In certain circumstances, the value of the peak power (PP) during a particular treatment cycle can be determined by a dedicated detector such as, for example, an RF Schottky Peak Detector sold by Linear Technology, Inc. The processor 1004 may reset the peak power detector at the onset of each new treatment cycle, for example. In certain instances, one or more of the various operational parameters recorded and stored in the memory 1006 can be stored in a condensed or compressed form, for example. In certain instances, the stored data can be compressed by consolidating the stored data in one or more histograms, for example. In certain instances, various data compression algorithms can be employed to compress the stored data, for example. In certain instances, some of the operational parameters of the surgical system 100 can be stored in high fidelity while others can be calculated from the data stored in high fidelity upon recovery of the stored data, for example. This practice can be desirable to save memory space, for example. In certain instances, the parameters recorded over time (t) in high fidelity can be voltage (V) and current (I), for example. In certain instances, the parameters recorded over time (t) in high fidelity can be impedance (Z) and current (I), for example. In certain instances, the parameters recorded over time (t) in high fidelity can be voltage (V) and impedance (Z), for example. The reader will appreciate that various unrecorded parameters may then be calculated from the recorded parameters, for example.

In any event, the peak power (PP) and/or the total energy (E) delivered to tissue during a particular treatment cycle can be communicated to the Processor 1004 which may store these values in dedicated columns in the database 1500, as illustrated in FIG. 14. In certain circumstances, tissue type, surgical procedure type, hospital information, user information, procedure location, and/or total procedure time, for example, can be provided by a user through a user interface 1022, as illustrated in FIG. 9A. In response, the processor 1004 may input these usage data to dedicated columns in the database 1500, as illustrated in FIG. 14. In certain circumstances, total operation time can be calculated by the processor 1004 by summing the time of all the treatment cycles, for example. The processor 1004 may enter the total operation time into a dedicated column in the database 1500, as illustrated in FIG. 14.

As described above, the processor 1004 can be configured to record, in the memory 1006, values of various operational parameters of the surgical system 100 during a plurality of treatment cycles performed by a surgical instrument of the surgical system 100 such as, for example, the ultrasonic device 104 and/or the RF surgical device 106. In certain circumstances, the processor 1004 can be configured to identify a subset of the stored values of the plurality of operational parameters which are temporally proximate to an intervening event. For example, as illustrated in module 1550 in FIG. 15A, the processor 1004 may store values of various operational parameters such as, for example, current (I), voltage (V), peak power (PP), energy expenditure (E), tissue impedance (Z), cycle time (T), end effector temperature, tissue type, procedure type, procedure time, operation time, hospital information, procedure location, and/or user information during a number of treatment cycles. In certain instances, the processor 1004 may store these operational parameters in the database 1500, for example. Upon detecting an intervening event such as, for example, an operational alert or error of the surgical instrument and/or the generator 102, the processor 1004 may be configured to identify a subset of the stored values of the operational parameters that are temporally proximate to the intervening event.

In certain instances, the processor 1004 may be configured to identify a subset of the stored values that preceded the intervening event in time, a subset of the stored values that coincided with the intervening event in time, and/or a subset of the stored values that followed the intervening event in time. In certain instances, the processor 1004 can be configured to identify a subset of the stored values that was recorded in a time period starting at, for example, 10 minutes prior to the intervening event and/or ending at, for example, 10 minutes past the intervening event. In certain instances, the processor 1004 can be configured to identify a subset of the stored values that was recorded in a time period starting at, for example, 5 minutes prior to the intervening event and/or ending at, for example, 5 minutes past the intervening event. In certain instances, the processor 1004 can be configured to identify a subset of the stored values that was recorded in a time period starting at, for example, 1 minute prior to the intervening event and/or ending at, for example, 1 minute past the intervening event. In certain instances, the processor 1004 can be configured to identify a subset of the stored values that was recorded in a time period starting at, for example, 10 seconds prior to the intervening event and/or ending at, for example, 10 seconds past the intervening event. The reader will appreciate that the time periods outlined above are exemplary time periods and that the processor 1004 can be configured to identify subsets of the stored values recorded in other time periods.

In certain circumstances, the processor 1004 can be configured to identify the subsets of the values of the various operational parameters stored in the memory 1006 and associated with an intervening event by highlighting these stored values in a particular color, for example. In certain circumstances, the processor 1004 may only retain certain subsets of the values of the various operational parameters stored in the memory 1006. For example, the processor 1004 may retain the subsets of the values of the various operational parameters stored in the memory 1006 that are associated with intervening events.

As described above, an intervening event that may trigger the processor 1004 to identify a subset of the stored values of the operational parameters of the surgical system 100 can be an operational error and/or alert of the surgical system 100. In at least one example, the intervening event can be an event that causes the surgical system 100 to reset, for example, by initiating a reset sequence. The processor 1004 can be configured to detect the initiation of the reset sequence and identify the subset of the stored values recorded in a time period starting at a time prior to the initiation of the reset sequence and/or ending at a time past the initiation of the reset sequence. In certain circumstances, the intervening event can be associated with one or more values of one or more of the operational parameters monitored during the operation of the surgical system 100. In certain instances, values of current (I), voltage (V), peak power (PP), energy expenditure (E), tissue impedance (Z), and/or cycle time (T) which fall outside predetermined ranges can be recognizable by the processor 1004 as intervening events. For example, the processor 1004 may receive one or more values of the measured tissue impedance (Z) that may be higher or lower than an acceptable range. In response, the processor 1004 can be configured to identify a subset of the stored values of the operational parameters of the surgical system 100 that is associated with such intervening events to permit examination of the circumstances surrounding these intervening events.

In certain circumstances, the processor 1004 can be configured to store sample values of various operational parameters such as, for example, current (I), voltage (V), peak power (PP), energy expenditure (E), tissue impedance (Z), end effector temperature, and/or time (T) during one or more treatment cycles performed by a surgical instrument of the surgical system 100 such as, for example, the ultrasonic device 104 and/or the RF surgical device 106. Storing sample values of the various operational parameters can reduce the size of the data stored in the memory 1006, for example. In certain instances, the sampling can be continuously performed throughout a treatment cycle. In certain instances, processing of the sampled data can be performed at the termination of a treatment cycle. In certain instances, processing of the sampled data can be performed at the termination of a surgical procedure. In certain instances, the processing of the sampled data can be performed in real-time through out a treatment cycle, for example.

In certain instances, the sampling may be performed by the processor 1004 at one or more designated parts of a treatment cycle, for example. In at least one example, the sampling may be performed by the processor 1004 at an initial segment of the treatment cycle. In at least one example, the sampling may be performed by the processor 1004 at an intermediate segment of the treatment cycle. In at least one example, the sampling may be performed by the processor 1004 at a final segment of the treatment cycle. In certain circumstances, the processor 1004 can be configured to sample and store, in the memory 1006, the total energy (E) delivered to the tissue at certain impedance ranges during a treatment cycle. These impedance ranges can include, for example, about 0 to about 4.99 ohms, about 5 to about 19.99 ohms, about 20 to about 99.99 ohms, about 100 to about 299.99 ohms, and/or greater than about 300 ohms, for example. The reader will appreciate that the processor 1004 can be configured to sample and store, in the memory 1006, values of various other operational parameters of the surgical system 100 during the abovementioned impedance ranges, for example.

Further to the above, the sampling can be performed by the processor 1004 in response to a triggering event. For example, one or more frequencies of the generator 102 can be triggering events. In such circumstances, the processor 1004 can be configured to perform the sampling while the generator 102 is at a particular frequency or in a range of frequencies during one or more treatment cycles performed by a surgical instrument powered by the generator 102 such as, for example, the ultrasonic device 104 and/or the RF surgical device 106. In at least one example, the processor 1004 may sample and store the measured values of, for example, current (I), voltage (V), peak power (PP), energy expenditure (E), and/or tissue impedance (Z) during a treatment cycle performed by the surgical instrument. In certain instances, the processor 1004 may sample the values of the various operational parameters described in the present disclosure at as sampling rate of about 20 HZ, for example. In certain instances, the sampling rate can be any sampling rate selected from a range of about 5 HZ to about 100 HZ, for example. In at least one example, the processor 1004 may sample and store the measured values of current (I), voltage (V), peak power (PP), energy expenditure (E), and/or tissue impedance (Z) during a treatment cycle performed by the surgical at a sampling rate of about 10 HZ, for example. Other sampling rates are contemplated by the present disclosure.

In certain circumstances, a surgical instrument of the surgical system 100 such as, for example, the ultrasonic device 104 and/or the RF surgical device 106 may include temperature sensors to measure, for example, the temperature of the jaws of the surgical instrument and/or the temperature of tissue captured by the jaws of the surgical instrument before, during, and/or after one or more of the treatment cycles performed by the surgical instrument. In certain instances, the processor 1004 can be configured to receive and store, in the memory 1006, the measured temperature of the jaws and/or the captured tissue. Such data may provide insight into the performance of the surgical instrument. A variety of other sensors can be utilized to provide the processor 1004 with data regarding various operational parameters of the surgical system 100. The sensors may include optical sensors, force sensors, and/or chemical sensors, for example. In certain instances, one or more force sensors such as, for example, strain gauges and load cells can be utilized to measure the force applied by the jaws of the surgical instrument against tissue captured by the jaws and/or the torque required to close the jaws. In certain circumstances, chemical sensors (typically done via gaseous head space analysis and/or spectroscopy) may test the composition of the smoke resulting during a treatment cycle performed by the surgical instrument. Such data can also be received and stored by the processor 1004 in the memory 1006 to provide insight into the performance of the surgical instrument.

In certain circumstances, as described above, the processor 1004 can be configured to store, in the memory 1006, some or all of the measured and/or calculated values of the various operational parameters of the surgical system 100 during one or more treatment cycles performed by the surgical system 100 such as, for example, current (I), voltage (V), peak power (PP), energy expenditure (E), tissue impedance (Z), and/or time (T). In other circumstances, the processor 1004 may store, in the memory 1006, statistical summaries of such values. Statistical summary data such as histogram data of the total energy expenditure (E) consumed per treatment cycle, for example, may be stored by the processor 1004 in the memory 1006. Such statistical data may provide insight into the performance the surgical instruments and can be useful for root causing failed surgical instruments, for example.

In certain instances, as described above, the processor 1004 may store values for various operational parameters of the surgical system 100 on the memory 1006. In certain instances, the memory 1006 can be housed within, attached to, and/or coupled to a surgical instrument of the surgical system 100 such as, for example, the ultrasonic device 104 and/or the RF surgical device 106. In certain instances, as described above, the data stored on the memory 1006 can be accessible wirelessly. In certain instances, for example, the data stored on the memory 1006 can be accessible via one or more wireless communication protocols such as, for example, IEEE 802.15.4 (ZigBee), IEEE 802.11a, IEEE 802.11b, IEEE 802.11g, IEEE 802.11n, IEEE 802.16a, IEEE 802.16g, Bluetooth or Infrared wireless communication protocols. In certain instances, the surgical instrument that houses the memory 1006 can be discarded at the completion of the surgical instrument's life cycle. For example, the surgical instrument can be dropped in a disposal container at the completion of the surgical instrument's life cycle.

Figure 19:
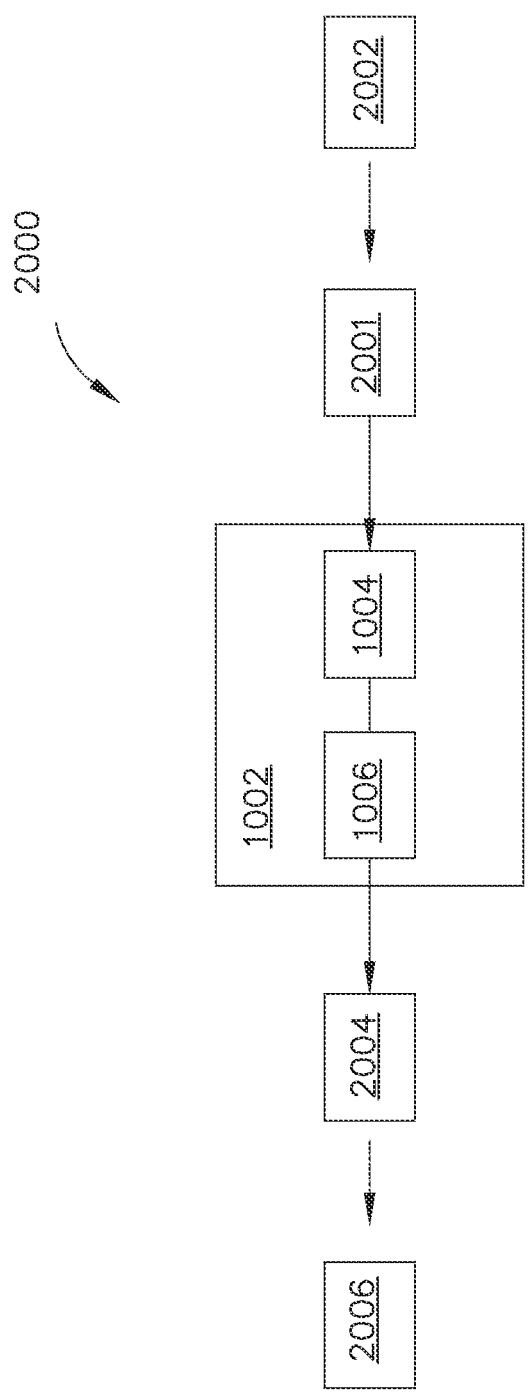
FIG. 19 a block diagram of a surgical system comprising a generator and a controller in accordance with certain embodiments described herein.

In certain instances, as illustrated in FIG. 19, a data transmission triggering module 2000 can be employed to initiate wireless transmission of the data stored on the memory 1006 at a triggering event, for example. In certain instances, the triggering event can be the dropping of the surgical instrument in the disposal container. The data transmission triggering module 2000 may include a Radiofrequency identification (RFID) receiver 2001; and the disposal container may include an RFID transmitter 2002. In certain instances, the processor 1004 can be operably coupled to the RFID receiver 2001 and can be configured to detect receipt of a triggering signal by the RFID receiver 2001 from the RFID transmitter 2002. In certain instances, the triggering signal can be limited in range such that the RFID receiver 2001 may be able to receive the triggering signal when the RFID transmitter 2002 in a predetermined proximity from the RFID receiver 2001. In certain instances, the triggering signal transmitted by the RFID transmitter 2002 can detected by the RFID receiver 2001 when the surgical instrument is dropped in the disposal container, for example. In response, the processor 1004 can be configured to activate a data transmitter 2004 configured to wirelessly transmit the data stored in the memory 1006 to a receiver 2006 which may deposit the stored data in an external storage device, for example, so that the stored data can be accessed and/or analyzed.

As described elsewhere in greater detail, the generator 102 can be powered by a battery. In certain circumstances, the generator 102 and the battery can be integrated with a surgical instrument such as, for example, the ultrasonic device 104 or the RF surgical device 106. In certain instances, the values of the total energy (E) consumption stored by the processor 1004 in the memory 1006 can be used to predict the battery's life cycle and/or optimize the battery performance in future designs. In certain instances, the stored values for the total energy (E) delivered during the treatment cycles performed by the surgical instrument can be analyzed, for example, by the manufacturer at the end of the instrument's life cycle to assess the battery's performance which can provide useful insight in optimizing battery design.

Further to the above, a processor such as, for example, the processor 1004 can be configured to predict the remaining battery life of a battery utilized with a surgical instrument such as, for example, the ultrasonic device 104 or the RF surgical device 106. In certain instances, the processor 1004 can be a battery life processor such as, for example, battery life processors bq34z100 and/or bq30z55-R1 EVM manufactured by Texas Instruments Inc. In certain instances, the processor 1004 may calculate the sum of the total energy (E) delivered during the treatment cycles performed by the surgical instrument. The processor 1004 may then estimate the remaining battery life from the calculated sum of the stored values of the total energy (E) and a stored value of the total energy in a full battery, for example. In certain instances, the processor 1004 may monitor and store the total energy (E) consumed from the battery prior to and/or up to a predetermined condition. In certain instances, the predetermined condition can be triggered when an alert is communicated to a user by the processor 1004 that the battery is nearly depleted, for example. In certain instances, the processor 1004 may record static battery voltage over time to assess battery capacity after known amounts of energy have been expended.

In certain instances, the processor 1004 can be configured to generate a signal to alert a user when the battery life is depleted to approximately 50% of its initial capacity, to approximately 30% of its initial capacity, to approximately 20% of its initial capacity, to approximately 10% of its initial capacity, to approximately 5% of its initial capacity, and/or to approximately 2% of its initial capacity, for example.

In certain circumstances, the processor 1004 can be configured to predict the number of complete treatment cycles that can be performed by the surgical instrument before the battery is depleted based on historical data of the total energy (E) consumed in previously performed treatment cycles. For example, the processor 1004 can be configured to estimate the total energy (E) consumption in a treatment cycle by averaging the total energy (E) consumed during previous treatment cycles. An estimate of the number of the remaining treatment cycles can then be calculated by the processor 1004 from the calculated remaining battery life and the estimated total energy (E) consumption in a treatment cycle. In certain instances, the processor 1004 can be employed to alert a user when the number of remaining treatment cycles reaches a predetermined threshold. For example, the processor 1004 may alert the user when the number of remaining treatment cycles reaches about 20 treatment cycles. For example, the processor 1004 may alert the user when the number of remaining treatment cycles reaches about 10 treatment cycles. For example, the processor 1004 may alert the user when the number of remaining treatment cycles reaches about 5 treatment cycles.

A method for predicting a battery life cycle of a battery configured to power a surgical instrument to treat tissue may comprise monitoring energy expenditure of the battery during each of a plurality of treatment cycles performed by the surgical instrument. The method may further comprise storing values of the monitored energy expenditure in a memory unit and calculating total energy expenditure from the stored values. The method may further comprise predicting remaining battery life from the calculated total energy expenditure.

As described herein, the processor 1004 can be configured to receive values of various operational parameters of a surgical system 100 such as, for example, the ultrasonic device 104 and/or the RF surgical device 106 during one or more treatment cycles performed by the surgical instrument. In certain instances, the processor 1004 can be configured to store such values, samples of such values, and/or statistical summary data of such values in a memory unit such as, for example, the memory 1006. In certain circumstances, the memory 1006 can be housed within the generator 102, for example. In other circumstances, the memory 1006 can be housed within the surgical instrument such as, for example, the ultrasonic device 104 or the RF surgical device 106, for example. In other words, each surgical instrument may include a memory unit to store the values, samples of the values, and/or statistical summary data of the values of the operational parameters of the surgical system 100.

Figure 15B:
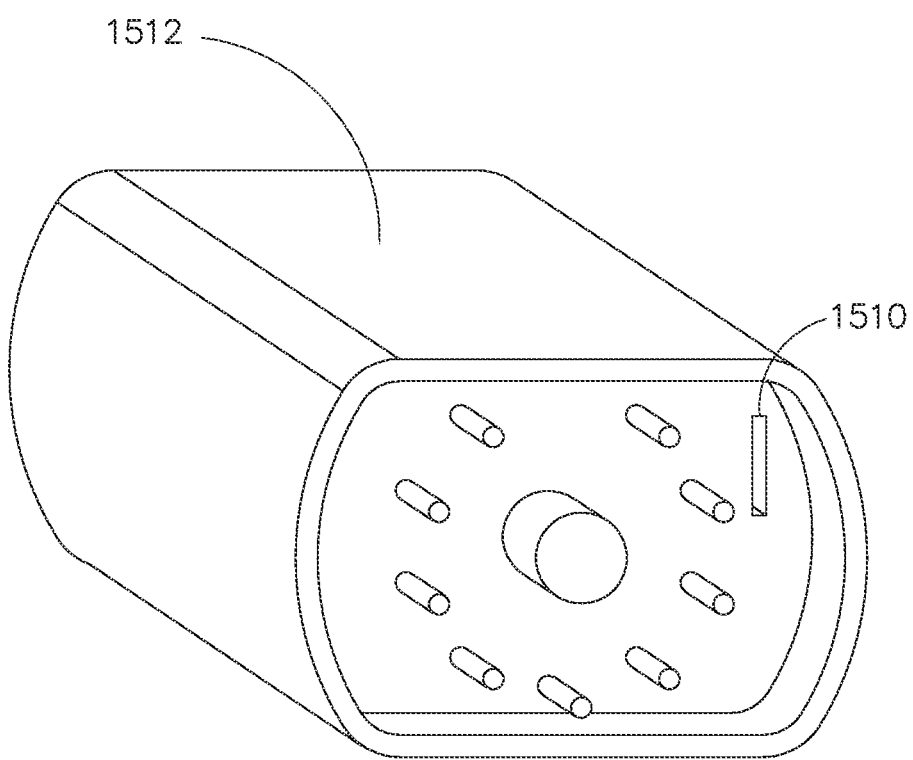
FIG. 15B illustrates a micro-usb connector for use with the system of FIG. 9A.

In certain circumstances, the memory 1006 can be removably coupled to the surgical instrument. For example, the memory 1006 may comprise a flash memory card which can be removably housed in a socket within the ultrasonic device 104 or the RF surgical device 106, for example. The data stored in the flash memory card can be recovered at the end of a surgical procedure and/or at the end of an instrument's lifecycle to analyze the stored data, for example. In certain instances, the memory 1006 can be accessible through an interface such as a universal serial bus (USB) interface or a micro-USB interface. For example, as illustrated in FIG. 15B, the memory 1006 can be accessible through a micro-usb connector 1510 located near a proximal end of an interface cable 1512 between the surgical instrument and the generator 102. In certain circumstances, the memory 1006 can be accessible through a micro-usb connector in a handle of the ultrasonic device 104 and/or the RF surgical device 106, for example.

Referring now to FIG. 16, illustrated is a module 1504 for use with the system 1000 to provide user specific performance feedback to a user of a surgical instrument such as, for example, the ultrasonic device 104 and/or the RF surgical device 106. The provided feedback can be based upon monitored operational parameters gathered by the processor 1004 and stored in the memory 1006 during use of the ultrasonic device 104 and/or the RF surgical device by the user. Such feedback may be beneficial in evaluating the user's performance and determining, for example, if the device is being used properly by the user.

As described above in greater detail, the processor 1004 can be configured to receive information about a user of the ultrasonic device 104 and/or the RF surgical device through the user interface 1022, for example, which can be stored in the memory 1006. Such information may include a user's name, an identification number, hospital information, surgical procedure type, and/or device type. As illustrated in FIG. 16, the processor 1004 can be configured to associate user identifying information, device identifying information, and/or surgical procedure identifying information with values of the operational parameters compiled during treatment cycles performed by the user. The processor 1004 may be configured to evaluate the user's performance by comparing the values of the operational parameters compiled during one or more treatment cycles performed by the user to preset normal standards stored in the memory 1006, for example, to determine whether the surgical instrument is being used properly. In at least one example, if one or more of the compiled values differ from the stored preset normal standards beyond an acceptable tolerance, the processor 1004 can be programmed to alert the user to improve the user's performance.

In some circumstances, the processor 1004 may compare the user's performance to historical usage data stored by the processor 1004 in the memory 1006 during previous treatment cycles performed by the user. In other circumstances, as illustrated in module 1506 in FIG. 17, the processor 1004 may compare a user's performance to performance of other users which may have been compiled by the processor 1004 and stored in the memory 1006 during previous usage of the instrument by the other users, for example. This may allow for evaluating the user's performance against the performance of other users under similar settings such as, for example, users in the same hospital and/or users performing the same or similar surgical procedures. In yet other circumstances, the processor 1004 may evaluate a user's performance against a combination of the preset normal standards and other users' performance. In any event, if the processor 1004 determines that the user's performance is not within an acceptable tolerance when compared to the preset normal standards (See FIG. 16) and/or other users' performance (See FIG. 17), the processor 1004 may issue a signal to inform the user of any issues with the user's performance and/or to suggest areas of improvement, for example.

As described above in greater detail, the processor 1004 can be configured to monitor and store treatment cycle duration time (T) and associate the duration time of a particular treatment cycle with user identification information such as, for example, the user's name and/or identification number which can be provided by the user through the user interface 1022, for example. In certain circumstances, actual treatment cycle duration time (Ta) can be controlled by the user who may end the treatment cycle prematurely or continue the treatment cycle past a preset recommended treatment cycle time (Tr) which can be stored in the memory unit 1006. The user may initiate a treatment cycle by signaling a processor such as, for example, the processor 1004 through the user interface 1022, for example, to activate the generator 102 to generate a therapeutic drive signal thereby causing current to pass through tissue captured by a surgical instrument such as, for example, the ultrasonic device 104 or the RF surgical device 106. At the completion of the treatment cycle, the user may terminate the treatment cycle by signaling the processor 1004, through the interface 1022, to deactivate the generator 102.

Referring to FIG. 18, illustrated is a module 1508 for use with the system 1000 (FIG. 9A) to evaluate a user's performance. The processor 1004 can be programed to compare the actual treatment cycle duration time (Ta) to the preset recommended treatment cycle time (Tr) to assess the user's compliance with the preset recommended treatment cycle time (Tr) for a particular treatment cycle. The user's compliance can be monitored over a number of treatment cycles N performed by the user and the processor 1004 may calculate the percentage of user compliance by calculating the percentage of treatment cycles where the user complied with the recommended time against the total number of cycles performed by the user. If the calculated percentage does not fall within an acceptable tolerance, the processor 1004 may be configured to issue a signal to instruct the user to comply with the recommended treatment cycle time (Tr), for example. In certain circumstances, the processor 1004 can be configured to store, in the memory 1006, the identification information for each of the users with a user compliance percentage that is lower than a threshold. The stored data can be recovered to provide such users with additional training, for example.

In certain circumstances, the acceptable tolerance can be based on a preset standard stored in the memory unity 1006. In other circumstances, the acceptable tolerance can be determined based on other users' performance such as, for example, users in the same hospital and/or users performing the same or similar surgical procedures. In yet other circumstances, the acceptable tolerance can be determined based on a combination of the preset standard and other users' performance.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, and application program interface (API), exchanging messages, and so forth.

Any patent, publication, or other disclosure material, in whole or in part, that is the to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is the to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A system for use with a surgical instrument, the system comprising:
   an end effector comprising a first and second electrode;
   a memory circuit to store computer-executable instructions for performing a biological material accumulation monitoring process; and
   a processor coupled to the memory circuit, the processor configured to execute the computer-executable instructions, wherein executing the computer-executable instructions causes the processor to:
   initiate a first treatment cycle;
   measure a first plurality of impedance values during the first treatment cycle;
   determine a first minimum impedance value for the first treatment cycle based on the measured first plurality of impedance values;
   compare the first minimum impedance value to a predetermined impedance threshold; and
   generate an alert in the event that the first minimum impedance value exceeds the predetermined impedance threshold.

2. The system of claim 1, wherein executing the computer-executable instructions further causes the processor to:
   initiate a second treatment cycle;
   measure a second plurality of impedance values during the second treatment cycle;
   determine a second minimum impedance value for the second treatment cycle based on the measured second plurality of impedance values;
   compare the second minimum impedance value to the predetermined impedance threshold; and
   generate an alert in the event that the second minimum impedance value exceeds the predetermined impedance threshold.

3. The system of claim 2, wherein executing the computer-executable instructions further causes the processor to:
   compare the first minimum impedance value and the second minimum impedance value; and
   generate an alert in the event that a difference between the first and second minimum impedance values exceeds a second predetermined threshold.

4. The system of claim 2, wherein executing the computer-executable instructions further causes the processor to:
   determine an average of the first minimum impedance value and the second minimum impedance value; and
   generate an alert in the event that the average exceeds a second predetermined threshold.

5. The system of claim 2, wherein executing the computer-executable instructions further causes the processor to:
   apply a non-therapeutic radio frequency signal to at least one of the first or second electrodes for measuring an impedance value.

6. The system of claim 2, wherein executing the computer-executable instructions further causes the processor to:
   apply a therapeutic radio frequency drive signal to at least one of the first or second electrodes for initiating a treatment cycle.

7. The system of claim 2, further comprising:
   a connector configured to access the memory circuit, wherein the connector is a micro-USB (universal serial bus) connector.

8. A surgical instrument comprising:
   an end effector comprising a first and second electrode;
   a memory circuit to store computer-executable instructions for performing a biological material accumulation monitoring process;
   a connector configured to access the memory circuit; and
   a processor coupled to the memory circuit, the processor configured to execute the computer-executable instructions, wherein executing the computer-executable instructions causes the processor to:
   initiate a first treatment cycle;
   measure a first plurality of impedance values during the first treatment cycle;
   determine a first minimum impedance value for the first treatment cycle based on the measured first plurality of impedance values;
   compare the first minimum impedance value to a predetermined impedance threshold; and
   generate an alert in the event that the first minimum impedance value exceeds the predetermined impedance threshold.

9. The surgical instrument of claim 8, wherein executing the computer-executable instructions further causes the processor to:
   initiate a second treatment cycle;
   measure a second plurality of impedance values during the second treatment cycle;
   determine a second minimum impedance value for the second treatment cycle based on the measured second plurality of impedance values;
   compare the second minimum impedance value to the predetermined impedance threshold; and
   generate an alert in the event that the second minimum impedance value exceeds the predetermined impedance threshold.

10. The surgical instrument of claim 9, wherein executing the computer-executable instructions further causes the processor to:
    compare the first minimum impedance value and the second minimum impedance value; and
    generate an alert in the event that a difference between the first and second minimum impedance values exceeds a second predetermined threshold.

11. The surgical instrument of claim 9, wherein the connector is a micro-USB (universal serial bus) connector.

12. The surgical instrument of claim 9, further comprising:

an ultrasonic transducer, wherein the end effector comprises an ultrasonic blade acoustically coupled to the ultrasonic transducer.

13. The surgical instrument of claim 9, wherein the first and second electrodes are configured to receive a therapeutic radio frequency drive signal.

14. A method of monitoring biological material accumulation onto an end effector of a surgical instrument, the surgical instrument comprising an end effector comprising a first and second electrode, a memory circuit, and a processor coupled to the memory circuit, the method comprising:
    initiating, by the processor, a first treatment cycle;
    measuring, by the processor, a first plurality of impedance values during the first treatment cycle;
    determining, by the processor, a first minimum impedance value for the first treatment cycle based on the measured first plurality of impedance values;
    comparing, by the processor, the first minimum impedance value to a predetermined impedance threshold; and
    generating, by the processor, an alert in the event that the first minimum impedance value exceeds the predetermined impedance threshold.

15. The method of claim 14, further comprising:
    initiating, by the processor, a second treatment cycle;
    measuring, by the processor, a second plurality of impedance values during the second treatment cycle;
    determining, by the processor, a second minimum impedance value for the second treatment cycle based on the measured second plurality of impedance values;
    comparing, by the processor, the second minimum impedance value to the predetermined impedance threshold; and
    generating, by the processor, an alert in the event that the second minimum impedance value exceeds the predetermined impedance threshold.

16. The method of claim 15, further comprising:
    comparing, by the processor, the first minimum impedance value and the second minimum impedance value;
    generating, by the processor, an alert in the event that a difference between the first and second minimum impedance values exceeds a second predetermined threshold.

17. The method of claim 15, further comprising:
    determining, by the processor, an average of the first minimum impedance value and the second minimum impedance value;
    generating, by the processor, an alert in the event that the average exceeds a second predetermined threshold.

18. The method of claim 15, wherein measuring an impedance value comprises applying a non-therapeutic radio frequency signal to at least one of the first or second electrodes.

19. The method of claim 15, wherein initiating a treatment cycle comprises applying a therapeutic radio frequency signal to at least one of the first or second electrodes.

20. The method of claim 15, wherein determining a minimum impedance value comprises applying a combination of a non-therapeutic radio frequency signal and a therapeutic radio frequency signal to at least one of the first or second electrodes.

* * * * *